(12) United States Patent
Cabrales et al.

(10) Patent No.: US 8,071,546 B2
(45) Date of Patent: Dec. 6, 2011

(54) USES OF PEGYLATED ALBUMIN

(75) Inventors: Pedro Cabrales, San Diego, CA (US); Amy Tsai, San Diego, CA (US); Seetharama A. Acharya, Cresskill, NJ (US); Belur N. Manjula, Cresskill, NJ (US)

(73) Assignees: La Jolla Bioengineering Institute, La Jolla, CA (US); Albert Einstein College of Medicine of Yeshiva University, Bronx, NY (US)

( * ) Notice: Subject to any disclaimer, the term of this patent is extended or adjusted under 35 U.S.C. 154(b) by 685 days.

(21) Appl. No.: 11/921,689

(22) PCT Filed: Jun. 9, 2006

(86) PCT No.: PCT/US2006/022619
§ 371 (c)(1),
(2), (4) Date: Nov. 20, 2008

(87) PCT Pub. No.: WO2007/058678
PCT Pub. Date: May 24, 2007

(65) Prior Publication Data
US 2010/0222260 A1    Sep. 2, 2010

Related U.S. Application Data

(60) Provisional application No. 60/689,205, filed on Jun. 10, 2005.

(51) Int. Cl.
*A61K 38/16* (2006.01)
*A61P 9/06* (2006.01)
*A61P 9/14* (2006.01)

(52) U.S. Cl. ............ 514/12; 530/350; 530/362; 424/9.1

(58) Field of Classification Search .................. 514/12; 530/362, 350; 424/9.1
See application file for complete search history.

(56) References Cited

U.S. PATENT DOCUMENTS

| | | | |
|---|---|---|---|
| 5,585,484 A | 12/1996 | Acharya et al. |
| 5,750,725 A | 5/1998 | Acharya et al. |
| 6,017,943 A | 1/2000 | Acharya et al. |
| 6,371,975 B2 | 4/2002 | Cruise et al. |
| 6,458,147 B1 | 10/2002 | Cruise et al. |
| 6,670,323 B1 | 12/2003 | Looker et al. |
| 6,773,613 B1 | 8/2004 | Winslow et al. |
| 6,844,317 B2 | 1/2005 | Winslow et al. |
| 6,875,423 B1 | 4/2005 | Intaglietta et al. |
| 7,019,117 B2 | 3/2006 | Acharya et al. |
| 7,038,016 B2 | 5/2006 | Talarico et al. |
| 7,144,989 B2 | 12/2006 | Acharya et al. |
| 7,169,900 B2 | 1/2007 | Acharya et al. |
| 7,271,145 B2 | 9/2007 | Winslow et al. |
| 7,501,499 B2 | 3/2009 | Acharya et al. |
| 7,521,174 B2 | 4/2009 | Acharya et al. |
| 2003/0009145 A1 | 1/2003 | Struijker-Boudier et al. |
| 2003/0161809 A1 | 8/2003 | Houston et al. |
| 2004/0002443 A1 | 1/2004 | Acharaya et al. |
| 2005/0026816 A1 | 2/2005 | Winslow et al. |
| 2005/0037966 A1 | 2/2005 | Ruben et al. |
| 2005/0159339 A1 | 7/2005 | Acharya et al. |
| 2005/0201988 A1 | 9/2005 | Acharya et al. |
| 2006/0111275 A1 | 5/2006 | Acharaya et al. |
| 2009/0215670 A1 | 8/2009 | Acharya et al. |
| 2009/0298746 A1 | 12/2009 | Acharya et al. |
| 2010/0216695 A1 | 8/2010 | Acharya et al. |

FOREIGN PATENT DOCUMENTS

WO   WO 2006/135740 A1   12/2006
WO   WO 2007/050121 A2   5/2007

OTHER PUBLICATIONS

Wettstein R et al., entitled "Resuscitation from Hemorrhagic Shock with MalPEG-Albumin: Comparison with MalPEG-Hemoglobin," Shock, vol. 22, No. 4, 2004, pp. 351-357.

"PCT Notification Concerning Transmittal of International Preliminary Report on Patentability" dated Mar. 19, 2009 issued by The International Bureau of WIPO in connection with PCT International Patent Application No. PCT/US2006/022619, 8 pages, Mar. 19, 2009.

*Primary Examiner* — Chih-Min Kam

(74) *Attorney, Agent, or Firm* — Amster, Rothstein & Ebenstein LLP

(57) ABSTRACT

The present invention is directed to uses of PEGylated albumins which include methods of treating reduced functional capillary density, reduced blood volume, septic shock and cardiac arrhythmia in a subject, which comprise administering to the subject a therapeutically effective amount of a PEGylated albumin.

27 Claims, 20 Drawing Sheets

USES OF PEGYLATED ALBUMIN

CROSS-REFERENCE TO RELATED APPLICATIONS

This application is a national stage entry under 35 U.S.C. §371 of PCT International Patent Application No. PCT/US2006/022619, filed on Jun. 9, 2006, which claims priority to U.S. Provisional Patent Application No. 60/689,205, filed on Jun. 10, 2005, the contents of which are hereby incorporated by reference.

STATEMENT OF GOVERNMENT SUPPORT

This invention was made with United States government support under USPHS grants R24-HL64395, HL62354, HL62318, HL-71064, HL-76182 and US Army Grant PR023085. Accordingly, the United States government has certain rights in this invention.

BACKGROUND OF THE INVENTION

Hypovolemic shock resulting from an acute loss of circulating blood volume is characterized by hypotension, tachycardia and oliguria. These parameters are used to assess the adequate efficacy of resuscitation fluids after trauma. However, they are insensitive to the existence of regional hypoperfusion, and conditions may appear "normal" even though occult tissue hypoxia may be present (Shoemaker et al., 1998). Using these traditional endpoints of resuscitation, hemorrhagic shock may appear to be 50-85% "compensated" although ongoing inadequate or impaired tissue perfusion can persist in different tissue localities (Porter and Ivatury, 1998). Suboptimal or inadequate resuscitation contributes to develop multiple organ failure and may ultimately result in death (Ivatury et al., 1996). Therefore there is significant interest in trying to identify more sensitive indicators of under-resuscitation and poor perfusion (Beilman et al., 1996; Powell et al., 1995; Sato et al., 1997; Zhang et al., 1996).

Skeletal muscle responds rapidly to acute blood loss and provides an easily accessible tissue site for monitoring the effects of hemorrhagic shock in experimental conditions (Cabrales et al., 2004, 2005; Kerger et al., 1996; Wettstein et al., 2004). In general these studies show that compensatory mechanisms such as vasoconstriction, activated during hemorrhage to maintain adequate tissue perfusion to vital organs, decrease blood flow in the microcirculation leading to impaired oxygen delivery and the generation of lactic acid via anaerobic glycolysis (Guyton 1996). Additionally, poor blood flow prevents the normal removal of carbon dioxide, which reacting with water forms high intracellular concentrations of carbonic acid (De Blasi et al., 1996; Guyton 1996; Rixen et al., 2002). The progressive increase of tissue acids and the concomitant reduction in bicarbonate lead to regional tissue acidosis, therefore monitoring skeletal muscle acid-base status should provide a sensitive means of assessing the severity of shock and the adequacy of resuscitation.

Accumulation of lactate tends to occur in conditions of oxygen depletion (ischemic hypoxia). Lactate is produced in skeletal muscle for glycolysis. Although skeletal muscle is the main producer of lactate in the body, lactate can also be taken up by skeletal muscle and used as a respiratory fuel. Lactate is a useful metabolic intermediate that can be exchanged between different cells within a given muscle, or exchanged between muscle and blood, and between muscle and other tissues (Aalkjier and Peng, 1997; Carsten 2001). The release and uptake of lactate is mediated mainly by monocarboxylate transporter. Lactate transport shows an obligatory 1:1 coupling between lactate and $H^+$ fluxes, and is therefore of great importance for pH regulation, especially during oxygen depravation or increased muscle activity (Aalkjier and Peng, 1997; Carsten 2001). The involvement of lactate/H+ cotransport in pH regulation is important for interstitial pH homeostasis, which may have important regulatory consequences, since the interstitial $H^+$ concentration may influence sensory nerve endings involved in the reflex regulation of blood flow and ventilation (Aalkjier and Peng, 1997; Carsten 2001).

Monitoring the microenvironment of skeletal muscle during shock is not a novel concept and previous investigators have demonstrated that changes in skeletal muscle $pO_2$, $pCO_2$, and pH levels occur rapidly after hemorrhage (Brantigan et al. 1974). However, monitoring tissue changes during shock and resuscitation is cumbersome and impractical. Optical techniques based on the use of low concentration pH-sensitive fluorescent dyes have been used successfully to measure pH (Moolenaar et al 1983), an in situ technology which should be well suited for analyzing tissue conditions during hemorrhage resuscitation to evaluate different fluids and procedures. This information is particularly relevant during evaluation of changes in oxygen delivery and release at the microcirculation using different plasma expanders, since pH affects the shape of the oxygen dissociation curve of hemoglobin via the Bohr effect. Tissue pH can be a powerful tool to easily establish a constitute index for aerobic and anaerobic metabolism of the tissue, specially on skeletal muscle where lactate and $H^+$ fluxes regulate pH.

Endotoxemia leading to sepsis is managed according to the "VIP" principles, namely Ventilate, Infuse and Pump (Weil and Shubin, 1969) on the basis that: 1) it is essential to maintain adequate tissue oxygenation; 2) administration of fluid is required to treat hypotension and maintain tissue perfusion; and, 3) central blood pressure should be maintained to support tissue perfusion following fluid resuscitation. Treatment according to these principles (Vincent et al, 2002) addresses systemic conditions and not necessarily problems at the microscopic functional level, leading to uncertain results as shown by the high morbidity and mortality associated with severe sepsis (Alberti et al., 2003).

Analysis of septic shock in the microcirculation has been inconclusive in identifying functional impairments that must be remedied, in part because of the difficulty of studying exposed microvascular preparations for extended periods. This problem is circumvented using chamber window models which allow analysis of the microcirculation for several days, showing conditions at the onset of sepsis, the response to treatment modalities, while monitoring systemic parameters. Microvascular studies show that maintenance of functional capillary density (FCD) is more critical for insuring survival during hemorrhagic shock than maintaining tissue $pO_2$ (Kerger et al., 1996). Decreased FCD follows capillary compression by tissue edema, endothelial swelling and plugging by leukocytes or red blood cell whose rigidity is increased due to endotoxemia (Nevière and Sibbald, 2000); however, FCD changes have not been extensively investigated in relation to sepsis.

Hdroxyethyl starch (HES) was found to maintain FCD but not NaCl (Hoffmann et al., 2002) in normotensive endotoxemia, and studies of capillary morphology show that microvascular surface area for $O_2$ exchange in septic sheep may be increased with infused colloids (Morisaki et al., 1994). Endotoxemia causes tissue hypoxia (Anning et al. 1999, Sair et al. 1996), which is reversed by fluid resuscitation but not by increased inspired $O_2$ ($F_1O_2$). Capillary $O_2$ extraction in sepsis is increased due to stopped flow in the rat skeletal muscle, suggesting that maldistribution of microvascular blood flow mismatches $O_2$ supply and demand (Ellis et al. 2002).

Maintenance or restoration of FCD should be important in the treatment of endotoxemia since the eradication of pathogens requires the delivery of antimicrobial agents through the circulation, an ineffectual process with decreased FCD.

SUMMARY OF THE INVENTION

The present invention provides a method of treating reduced functional capillary density in a subject which comprises administering to the subject an amount of a PEGylated albumin effective to treat reduced functional capillary density in the subject.

The present invention also provides a method of treating reduced blood volume in a subject which comprises administering to the subject an amount of a PEGylated albumin effective to treat reduced blood volume in the subject.

The present invention further provides a method of treating septic shock in a subject which comprises administering to the subject an amount of a PEGylated albumin effective to treat septic shock in the subject.

The present invention still further provides a method of treating cardiac arrhythmia in a subject which comprises administering to the subject an amount of a PEGylated albumin effective to treat cardiac arrhythmia in the subject.

DETAILED DESCRIPTION OF THE INVENTION

Figure 1:
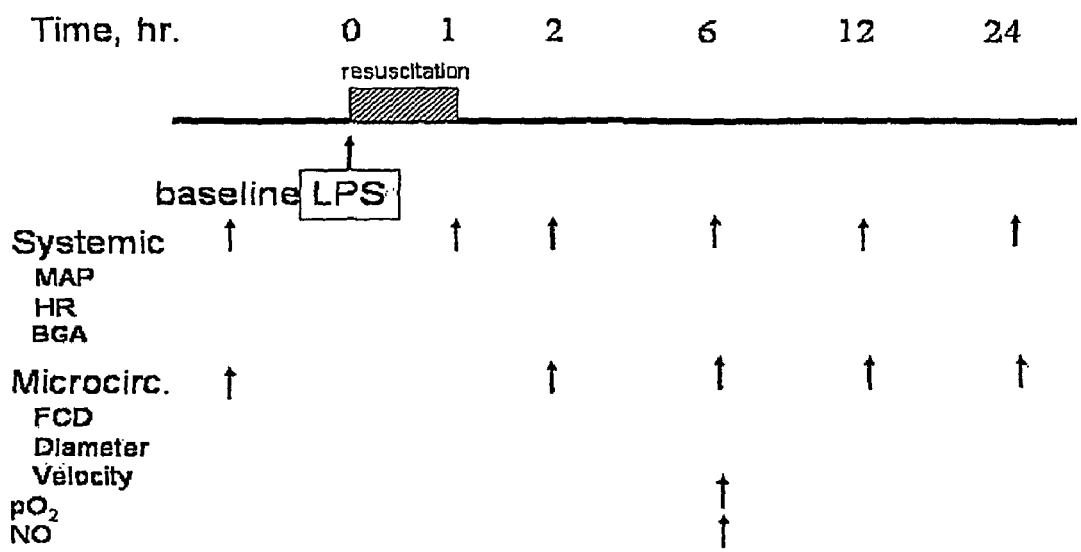
FIG. 1. Baseline measurements were taken before injection of lipopolysaccharide (LPS) at time point t=0. Resuscitation was initiated 10 min after injection of LPS and continued for one hr. Systemic and microvascular parameters were measured at each time point. $PO_2$ and perivascular NO concentration was measured at t=6 hr for the no resuscitation, dextran and PEG-BSA-24 groups.

The present invention is directed to uses of PEGylated albumins, wherein the pegylated albumin comprises a polyethylene glycol (PEG) conjugated to albumin. As used herein, "pegylation" means linking to PEG, and a "pegylated" albumin is an albumin attached to PEG.

The present invention provides a method of treating reduced functional capillary density in a subject which comprises administering to the subject an amount of a PEGylated albumin effective to treat reduced functional capillary density in the subject. The subject, for example, may have endotoxemia, sepsis, septic shock, a reduced blood volume, a cardiac arrhythmia, and/or be undergoing surgery.

The present invention also provides a method of treating reduced blood volume in a subject which comprises administering to the subject an amount of a PEGylated albumin effective to treat reduced blood volume in the subject. Prior to treatment with PEGylated albumin, the subject may have lost, for example, up to 75% of red blood cell mass, for example, between 50% and 75% of red blood cell mass.

The present invention further provides a method of treating septic shock in a subject which comprises administering to the subject an amount of a PEGylated albumin effective to treat septic shock in the subject.

Preferably, the PEGylated albumin is administered within 2 hours following the onset of septic shock or reduced blood volume.

The present invention still further provides a method of treating cardiac arrhythmia in a subject which comprises administering to the subject an amount of a PEGylated albumin effective to treat cardiac arrhythmia in the subject. The cardiac arrhythmia may be a ventricular arrhythmia and/or an atrial arrhythmia. The subject may be undergoing surgery.

As used herein, to "treat" a condition means to reduce or eliminate the severity and/or frequency of a sign or symptom of the condition.

The present invention also provides a method of treating a subject which comprises administering PEGylated albumin to the subject. The subject may, for example, have a cardiac arrhythmia.

PEGylated albumins disclosed herein can also be used in a subject to transport nitric oxide (NO) and to scavenge free radicals. Thiol groups of the PEGylated albumin can transport NO as S-nitroso derivatives. Free radicals can be scavenged by having covalently bound nitroxyl radicals. These are distinct from the S-nitroso derivatives of thiols, which form a reversible complex.

The albumin used may be, for example, human serum albumin or bovine serum albumin, or another appropriate mammalian albumin.

The concentration of PEGylated albumin administered to the subject may be 1.5 g/dL-5.0 g/dL, preferably 2.5 g/dL. The PEGylated albumin may be administered, for example, at a dose of 16 to 30 ml/kg body weight/hr, preferably at about 24 ml/kg body weight/hr. The exact dosage required for an individual subject can be readily determined by a physician skilled in the art.

In one embodiment, the PEGylated albumin has a molecular weight of about 130 kDa. In one embodiment, the PEGylated albumin has a molecular radius of 8-9 nm. There may be between 6-18 PEG chains conjugated to albumin. In a preferred embodiment, 12 PEG chains are conjugated to albumin. Each PEG chain may have a molecular weight of 200 daltons to 20,000 daltons, preferably 3,000 to 5,000 daltons, and more preferably 5,000 daltons. PEGs of various molecular weights, conjugated to various groups, can be obtained commercially, for example from Nektar Therapeutics, Huntsville, Ala.

Preferably, the PEGylated albumin has a colloid osmotic pressure of 37-40 mm Hg. Preferably, the PEGylated albumin has a viscosity of 2.0 to 4.0 cP.

The polyethylene glycol (PEG) may be, for example, a maleimide PEG, an alkylamide PEG, an iodoacetamide PEG, a p-nitro thio-phenyl PEG, a vinyl sulfone PEG, or a mixed disulfide PEG. The maleimide PEG may be, for example, a maleimide phenyl PEG or a maleimide PEG comprising an alkyl linker.

The PEG can be attached to the albumin via a linker and/or an extension arm. As used herein, an "extension arm" refers to the carbon chain-thiol group that is attached to albumin during a thiolation process. The extension arm places the thiol group away from the surface of the albumin, thereby enhancing the accessibility of the thiol group to bulky PEG reagents. The linker may comprise an alkyl, aryl and/or heteroaryl group. For example, the alkyl group can be a propyl group, and the aryl group can be a phenyl group. The linker or extension arm may comprise a δ-mercapto butyrimidyl chain or a γ-mercapto propylamide chain.

The PEGylated albumin can comprise a polyethylene glycol (PEG) attached to a thiolated amino group of albumin, wherein the amino group is thiolated using dithiobis(sulfosuccinimidyl propionate) (DTSSP) or dithiobis(succinimidyl propionate) (DTSP) or dithiobispropionimidate.

In one embodiment, PEGylation does not alter the surface charge of albumin.

The PEGylated albumins may be provided in a composition comprising a pharmaceutically acceptable carrier. Pharmaceutically acceptable carriers include, but are not limited to, additive solution-3 (AS-3), saline, phosphate buffered saline, Ringer's solution, lactated Ringer's solution, Locke- Ringer's solution, Kreb's Ringer's solution, Hartmann's balanced saline solution, and/or heparinized sodium citrate acid dextrose solution. The pharmaceutical compositions may be administered by conventional means including but not limited to transfusion and injection.

The present invention is illustrated in the following Experimental Details section, which is set forth to aid in the understanding of the invention, and should not be construed to limit in any way the scope of the invention as defined in the claims that follow thereafter.

The specific experimental examples presented herein have been carried out using a defined composition of PEG-albumin generated using thiolation mediated maleimide chemistry based PEGylation. The viscosity and the colloidal osmotic pressure of PEGylated albumin has been hypothesized as the primary properties responsible for these applications. Other PEG albumins could also be used for these procedures, for example, PEGylated albumins with other amounts of PEG generated by the same procedures or by another thiolation mediated PEGylation protocol or PEG-albumin generated using for example isothiocyanate chemistry based PEGylation.

EXPERIMENTAL DETAILS

Example 1

Treatment of Endotoxemia Using Peg-Albumin

I. Introduction

The present study was carried out to test the hypothesis that recovery from endotoxemia according to the "VIP" approach is improved by restoring functional capillary density (FCD). Endotoxemia was induced by the administration of lipopolysaccharide (LPS) in a dosage that produced a maximal reduction in FCD, without being lethal. Hypervolemic infusion of PEG-BSA was used as a plasma expander, and compared with no treatment and with dextran 70 kDa treatment as a means of restoring FCD.

II. Materials and Methods

Animal Preparation. Investigations were performed in the golden Syrian hamsters (Charles River Laboratories, Boston, Mass.) window chamber model following guidelines in the *Guide for the Care and Use of Laboratory Animals* (National Research Council, 1996), and surgical techniques previously described (11), and approved by the local Animal Subjects Committee. Briefly, the chamber is positioned and implanted under anesthesia (50 mg/kg ip injection, Nembutal, Abbott, Abbott Park, Ill.). A chamber consists of two titanium frames with 15-mm circular windows showing a thin layer of retractor muscle in the glass protected side and the intact subcutaneous skin on the opposing side exposed to the ambient environment. The animal recovers in 2 days and if the chamber tissue shows no edema, bleeding, or unusual neovascularization, the animal is re-anesthetized for implantation of arterial and venous catheters (PE-50) in the carotid artery and jugular vein. Catheters filled with heparinized saline (30 IU/ml) are tunneled under the skin and exteriorized at the dorsal side of the neck and attached to the chamber frame with tape. Experiments are performed between 24 h and 48 h after catheter implantation.

Inclusion Criteria. Animals were suitable for the experiments if their systemic parameters were within normal range: 1) heart rate (HR)>320 beats/min; 2) mean systemic blood pressure (MAP)>80 mmHg; 3) systemic hematocrit (Hct)>45%; 4) systemic arterial $pO_2$>50 torr. Animals were excluded from the study if the chamber tissue examined under low (150×) and high (650×) magnification showed sign of edema and/or bleeding.

Systemic Parameters. MAP and HR were monitored over the entire experimental period (Biopac, Santa Barbara, Calif.; Spectramed Pressure Transducer). Systemic hematocrit (Hct) was measured from centrifuged arterial blood sample taken in heparinized capillary tubes (Readacrit Centrifuge, Clay Adams, Division of Becton and Dickinson, Parsippany, N.J.).

PEG-BSA. Bovine serum albumin (BSA) was conjugated with PEG using a single step version of the thiolation mediated, maleimide chemistry based conservation PEGylation described by Acharya et al. (1996). BSA (0.25 mM) (Sigma-Aldrich, St. Louis, Mo.) was incubated overnight with 5 mM 2-iminothiolane (BioAffinity Systems, Rockford, Ill.) and 7.5 mM maleimide phenyl PEG-5000 in phosphate buffer saline (PBS). The surface amino groups are thiolated, and thiol groups generated on the protein in situ are derivatized by the maleimide PEG in the reaction mixture. The single step reaction limits the oxidation of the thiols of the thiolated protein to generate dimers and polymers of BSA, and is the preferred approach to generate PEGylated proteins. Excess reagents were removed by tangential flow filtration using the Minim System (Pall Life Sciences, Ann Arbor, Mich.) after overnight incubation. A 70 kDa membrane was used for diafiltration for removal of unreacted PEG and excess iminothiolane and PEG-BSA was concentrated to 2.5 gms/dL (protein based). This process yielded an average of 12 copies of PEG 5K chains conjugated to a BSA molecule, a molecular weight of 130 kDa and a molecular radius of 8-9 nm.

Blood Chemistry. Arterial blood sampled from the carotid artery catheters into heparinized capillary tubes was analyzed for $pO_2$, $pCO_2$ and pH at 37° C. (pH/Blood Gas Analyzer, Model 248, Bayer, Tarrytown, N.Y.). Hemoglobin concentration was measured using the B-Hemoglobin, (Hemocue, Sweden).

Microhemodynamic Parameters. Arteriolar and venular diameter (D) and blood flow velocities were measured on-line (Photo Diode/Velocity Tracker Model 102B, Vista Electronics, San Diego, Calif.) (13). The measured centerline velocity was corrected according to vessel size (V) and blood flow (Q) was calculated from $Q=V \times \pi (D/2)^2$.

Arterioles and Venules. Arterioles and venules were grouped into large feeding arterioles (A1) and small arcading arterioles (A2) and large venules (V1) and small collecting venules (Vc) (14). The diameter of arterioles with vasomotion was averaged during a one minute interval. The same vessels were studied throughout an experiment.

Functional Capillary Density (FCD). Functional capillaries have red blood cells (RBCs) transit during a 45-second period. FCD was tabulated from the capillary lengths with RBC transit in an area comprising 10 successive microscopic fields (420×320 $\mu m^2$). FCD ($cm^{-1}$) is the total length of RBC-perfused capillaries divided by the area of the microscopic field of view.

Microvascular $pO_2$ Distribution. Oxygen tension measurements were made using the oxygen-dependent phosphorescence quenching method (15, 16). Animals receive a slow intravenous injection of 15 mg/kg body weight (10.1 mg/ml) of a Palladium-meso-tetra(4-carboxyphenyl) porphyrin (Porphyrin Products, Inc., Logan, Utah) and measurements are made 10 minutes after injection. Intravascular measurements are made from an optical rectangular window (5 $\mu m \times 40$ $\mu m$) parallel to the vessel wall: Tissue $pO_2$ measurements are obtained from an optical window (6×6 $\mu m$) placed in intercapillary spaces in regions void of large vessels. Decay curves are analyzed off-line, using a standard single exponential least squares numerical fitting technique and the resultant time constant is applied to the Stern-Volmer equation (16) to calculate $pO_2$, using parameters corrected for this animal model.

Oxygen Saturation Curve for Hamster Blood. The oxygen saturation curve for hamster blood was determined using a Hemox Analyzer (TCS Corp., PA) using freshly collected blood.

Perivascular Nitric Oxide (NO) Concentration Measurement. The nanomolar NO concentration was measured using carbon fiber electrodes (Carbostar-1, Kation Scientific, Minneapolis, Minn.). Three coatings of Nafion were applied to the tip of the electrodes (5% in aliphatic alcohols, Sigma-Aldrich, St. Louis, Mo.) to repel active anions (e.g, nitrate, nitrite and ascorbate) (17). The microelectrodes were polarized at +0.8 V relative to a silver-silver chloride reference electrode (ee009, Cypress Systems, Lawrence, Kans.). NO measurements were performed using a working and reference electrode system, and the current generated was measured with a potentiostat and a Keithley Electrometer-Amplifier model 610C (Cleveland, Ohio). The microelectrodes were calibrated with standard gas mixtures of NO and nitrogen, had a linear current-NO relationship and 0 nM NO currents were in the range of 5-10 pA. Microelectrodes generated >1 pA/1,000 nM NO and had a 30 sec time constant in the tissue. The cover glass of the window chamber was removed at the completion of the microhemodynamics measurements at 6 hours after LPS injection and the tissue preparation was superfused (~5 ml/min) with a physiological salt solution of the following composition (in mM): 131.9 NaCl; 4.7 KCL; 2.0 $CaCl_2$; 1.2 $MgSO_4$ and 20.0 $NaHCO_3$, with pH 7.4 at 37° C. The tissue was maintained at 33-34° C. by the heated solution. The solution spread on the tissue as a thin film, drained into a platter, and was drawn off by suction. The solution was equilibrated with 95% $N_2$ and 5% $CO_2$, which maintained suffusate pH at 7.4 and minimized $O_2$ delivery from the superfusate to the tissue (18, 19). NO measurements were initiated 20 minutes after glass window removal, a period in which the tissue stabilized and showed constant microvascular parameters (20).

Perivascular measurements were made by penetrating the perivascular tissue with the microelectrode using a micromanipulator to place the tip as close as possible to the microvessel without indenting the wall. A long working distance objective 10× Leitz (0.33 n.a., 10×) was used to direct the electrode to the measurement site. As in the studies of Nase et al. (21), measurements were taken of the highest possible NO concentration for a given vessel.

Oxygen Delivery and Extraction. The rate of oxygen released by blood to the tissue of the hamster window preparation was calculated according to the formulation of Sakai et al. (22):

$$O_{2\ delivery} = RBC\ Hb \times \Delta_{A-V} \%\ saturation\ RBC \times Q$$

where RBC Hb is the concentration of hemoglobin in red blood cells, $\Delta_{A-V}$% saturation is the arteriolar-venular difference in oxygen saturation of red blood cells and plasma hemoglobin respectively, and Q is the venular flow. In all cases the blood oxygen content was determined by using the oxygen dissociation curve for hamster blood to calculate the oxygen content at the measured blood $pO_2$. Data on oxygen saturation were obtained as previously described (23), and microvascular hematocrit was corrected according to Lipowsky and Firrell (24).

Shear rate. Wall shear rate was defined by $WSR = 8\ VD^{-1}$.

Experimental Protocol. Animals were placed in a plexiglas restraining tube fixed to the stage of the intra-vital microscope (IMT-2 OLYMPUS). The animals were given 30 min to adjust to the tube environment before the baseline systemic and microcirculatory parameters were measured. Immediately after baseline measurement sepsis was induced by intravenously injecting lipopolysaccharide (LPS) from *Escherichia Coli*, serotype 0128:B12 (Sigma, St. Louis, Mo.), intravenously (t=0). To determine LPS dosages, animals were divided into 2 groups receiving 2 mg/kg of LPS (LPS-L) and 4 mg/kg of LPS (LPS-H). Resuscitation was initiated approximately 10 minutes after LPS administration and infused intravenously during 1 hour. Systemic parameters were measured at t=1, 2, 6, 12 and 24 hrs after LPS injection, and microcirculatory parameters were measured at 2, 6, 12 and 24 hrs after LPS injection (FIG. 1). Animals were returned to their housing with free access to food and water between measurement sessions.

After administration of LPS, animals were randomly divided to the following four groups: 1) No resuscitation, animals only receiving LPS without resuscitation (NR); 2) Dextran 70, animals resuscitated with Dextran 70 (6% wt/vol mean molecular weight, 70 kDa, COP 49.9 mmHg and 2.8 cp viscosity, Braun Medical, Irvine, Calif.) infused at 16 ml/kg hr (Dex); 3) PEG-Bovine serum albumin (2.5% wt/vol, COP 37.6 mmHg and 2.0 cp viscosity, Albert Einstein College of Medicine, Bronx, N.Y.) infused at 16 ml/kg hr (PEG-BSA-16); 4) PEG-BSA (2.5% wt/vol, Albert Einstein College of Medicine, Bronx, N.Y.) infused at 24 ml/kg hr (PEG-BSA-24).

$PO_2$ measurements and perivascular and tissue NO concentration measurements were made in different groups of hamsters 6 hours after LPS injection. Systemic and microhemodynamic parameters were measured at each time point and at baseline. For oxygen measurements animals were grouped as NR, Dex, and PEG-BSA-24. Measurements of NO concentration were carried out in two independent groups of animals randomly divided into NR and PEG-BSA-24.

Animals were returned to their housing with free access to food and water between measurement sequences.

Data Analysis. Results are presented as mean±SD unless otherwise noted. All measurements were compared with baseline, and compared between each group at the same time point. Data are presented as absolute values and ratios relative to baseline values. A ratio of 1.0 signifies no change from baseline, while lower and higher numbers are indicative of changes respectively higher and lower than baseline.

Statistical analysis was performed using GraphPad Prism 4.01 (GraphPad Soft Ware, Inc., San Diego, Calif.). Differences between two means was assessed using the t-test. Comparison between three or more means was performed using one-way ANOVA and when appropriate post hoc analysis was performed with Newman-Keuls multiple comparison test. Changes were considered statistically significant if p<0.05. The traditional power analysis is not applicable to these studies because these experiments in general have a large variability and to obtain an appropriate power it would require a large number of animals. In this study, because of the complicated and lengthy procedure and the requirement to minimize animal usage due to the regulations of the Animal Usage Policies, power was not calculated. However, this does not preclude finding that the data are statistically significantly different.

III. Results

Figure 2:
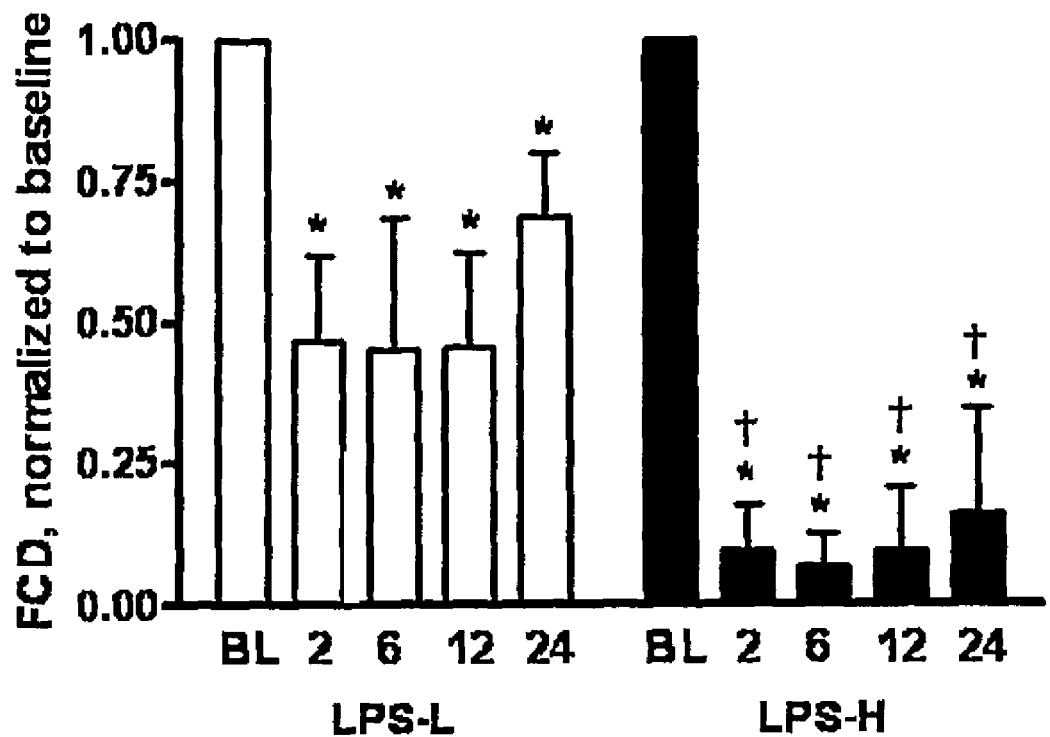
FIG. 2. Experiments to determine the maximum non-lethal dosage that would cause the most significant change in FCD. Effect of using 2 mg/kg LPS-L (n=5), or 4 mg/kg LPS-H (n=4). The LPS-H dosage provided a significantly greater depression of FCD at all time points and was used in the study. FCD in the LPS-L group was reduced by 49±17% (t=2 hr), 30±14% (t=6 hr), 51±15% (t=12 hr) and 69±13% (t=24 hr) from baseline, being significantly lower than baseline at all time points. FCD in the LPS-H group was reduced to 10±8% (t=2 hr), 7±6% (t=6 hr), 9±11% (t=12 hr) and 16±18% (t=24 hr) of baseline, being significantly different from baseline at all time points.

Sepsis Model, Studies to Determine LPS Dosage. Eight animals divided into two groups of 4 were used for the analysis of LPS dosage. At baseline MAP of the LPS-L group and LPS-H group were not significantly different. MAP at t=6, 12 and 24 hours (hr) was significantly decreased to 80%, 73% and 86% in the LPS-H group relative to baseline. At t=6 hr, MAP in the LPS-L group was 92% of baseline, which was statistically higher than the LPS-H group, and there were no significant differences between these two groups at other time points. HR at t=6 hr was reduced to 90% of baseline in the LPS-H group, being significantly lower than the LPS-L group which increased to 121% of baseline. Changes in FCD after LPS injection are shown in FIG. 2. FCD was reduced significantly in the LPS-H group relative to the LPS-L group at all time points after LPS injection. The higher LPS dosage of 4 mg/kg was selected for the present studies (LPS-H) since this produced the maximal decrease in FCD without lethality.

Resuscitation Study, Systemic Parameters. Sixteen animals were studied, 4 animals randomly assigned to each group. MAP for the different groups are given in Table 1 showing that there was no significant difference between groups at baseline. Upon induction of endotoxemia, MAP was significantly lower in the NR group vs. baseline at t=6 and 12 hr. In Dex and both PEG-BSA groups there were no significant MAP changes during the experimental period. MAP was significantly lower in NR than in treatment groups at t=6 and 12 hr.

Changes in HR are given in Table 1. There were no differences from baseline and between each group at any time point.

There was no statistical difference in systemic parameters between groups undergoing fluid resuscitation with either of the 3 resuscitation modalities; however, there was a significant difference among all treated groups and the NR group.

Microcirculation. RBC aggregation was observed in the NR group and the Dex group, but not in the PEG-BSA groups. In the NR group some arterioles had no flow at t=6, 12 and 24 hr, and some venules had no flow at t=2, 6, 12 and 24 hr. In the Dex group some arterioles had no flow at t=2 hr, and some venules had no flow at t=2, 6 and 12 hr. Flow was present in all arterioles and venules in the PEG-BSA treated groups.

Figure 3:
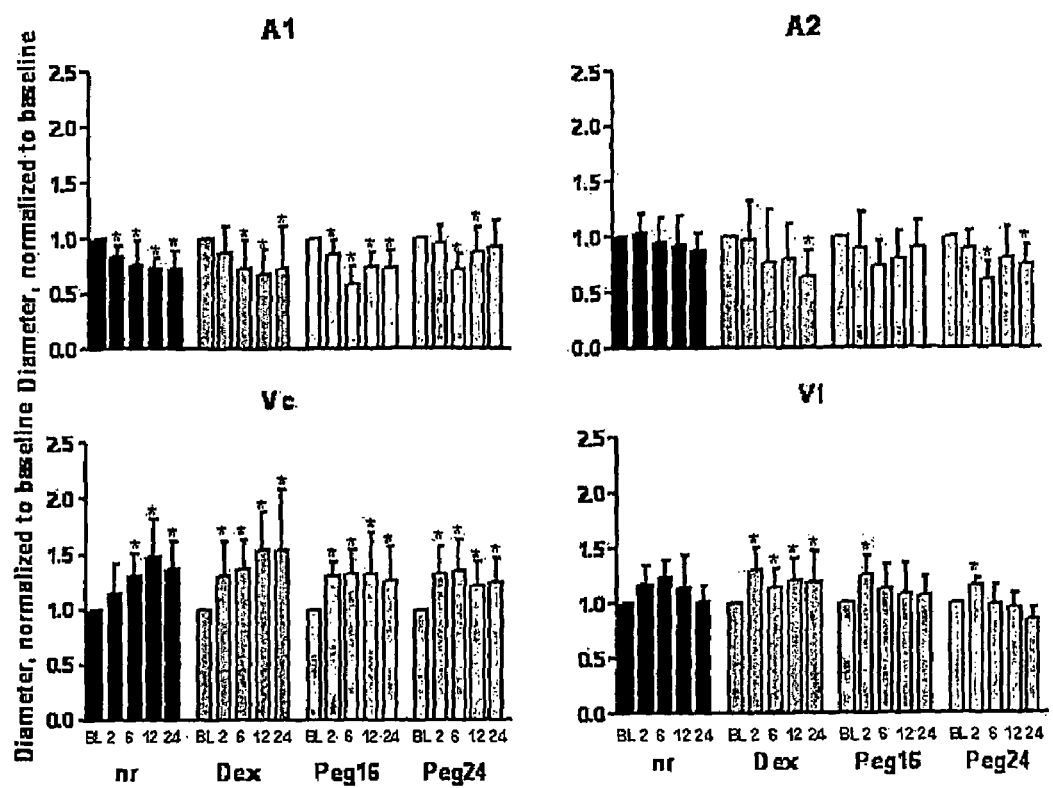
FIG. 3. Changes in microvascular diameter as a function of no treatment and treatment of endotoxemia due to infusion of 4 mg/kg of LPS. Dex: animals resuscitated with Dextran 70 (6% wt/vol) infused at 16 ml/kg hr (Dex); PEG-16: Resuscitation with PEG-BSA (2.5% wt/vol), infused at 16 ml/kg hr. PEG-24: Resuscitation with PEG-BSA (2.5% wt/vol hr) infused at 24 ml/kg hr (PEG-BSA-24). Absolute values of vessel diameters are as follows: in NR group; A1, 65±16 µm (n=6), A2, 34±7 µm (n=6), Vc, 54±18 µm (n=8), V1, 136±34 µm (n=4), in Dex group; A1, 62±25 µm (n=11), A2, 38±12 µm (n=9), Vc, 44±10 µm (n=10), V1, 95±24 µm (n=11), in PEG-BSA-16 group, A1, 59±12 µm (n=9), A2, 35±8 µm (n=9), Vc, 48±14 µm (n=13), V1, 122±37 µm (n=6), in PEG-BSA-24 group, A1, 61±13 µm (n=14), A2, 39±12 µm (n=5), Vc, 49±25 µm (n=14), V1, 119±46 µm (n=6). *p<0.05 vs. baseline.

Changes in vessel diameter are shown in FIG. 3 normalized relative to baseline. A1 diameters were below baseline for all groups, while A2 vessels did not show any major trend. Vc venules were mostly dilated in all groups, while V1 vessel in most cases were not statistically different from baseline.

Figure 4:
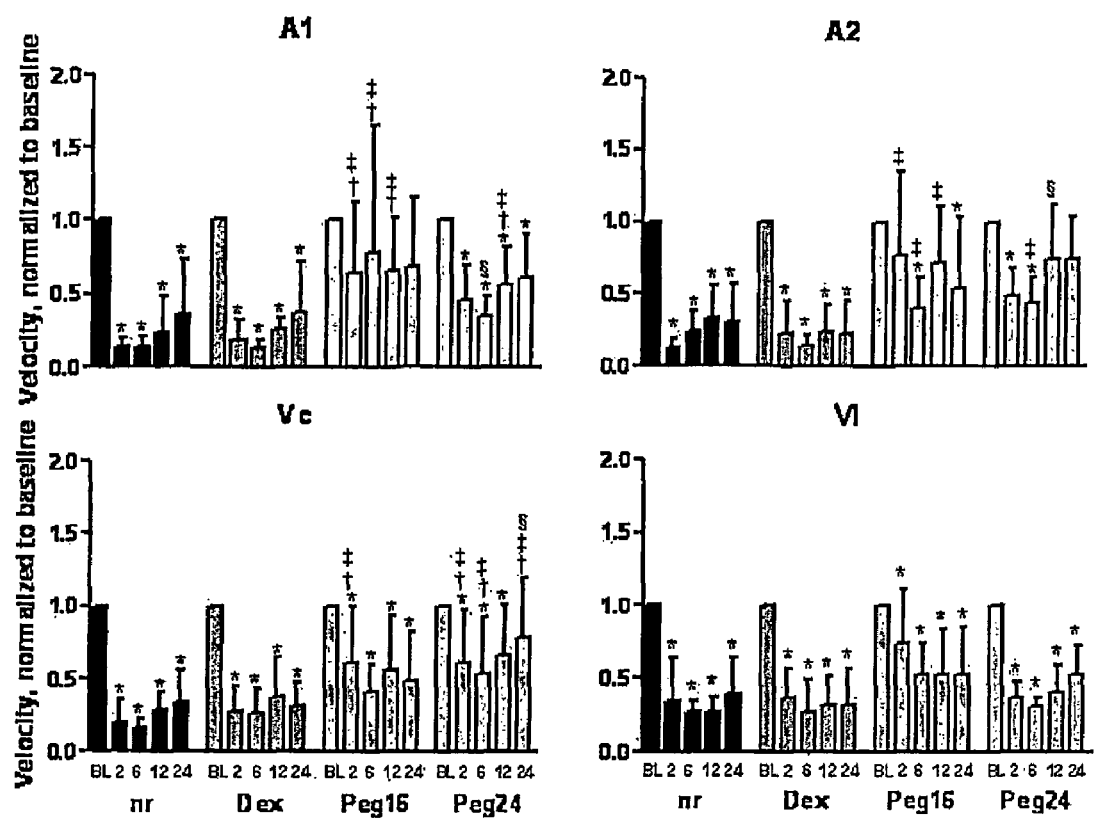
FIG. 4. Red blood cell flow velocity in the microcirculation for the groups of FIG. 3 normalized to baseline. Absolute values of RBC velocity at baseline are as follows: NR group: A1, 5.6±1.9 mm/s, A2, 4.2±1.0 mm/s, Vc, 3.0±1.0 mm/s, V1, 3.4±1.6 mm/s; Dex group: A1, 6.6±2.0 mm/s, A2, 5.0±1.4 mm/s, Vc, 2.0±0.9 mm/s, V1, 2.6±1.0 mm/s; PEG-BSA-16 group: A1, 5.3±3.0 mm/s, A2, 4.7±1.8 mm/s, Vc, 2.2±0.9 mm/s, V1, 2.9±1.4 mm/s: PEG-BSA-24 group: A1, 7.4±2.6 mm/s, A2, 5.8±2.4 mm/s, Vc, 3.1±1.1 mm/s, V1, 3.6±1.0 mm/s. *p<0.05 vs. baseline; †p<0.05 vs. NR group; ‡p<0.05 vs. Dex group; § p<0.05 vs. PEG-BSA-16 group.
Figure 5:
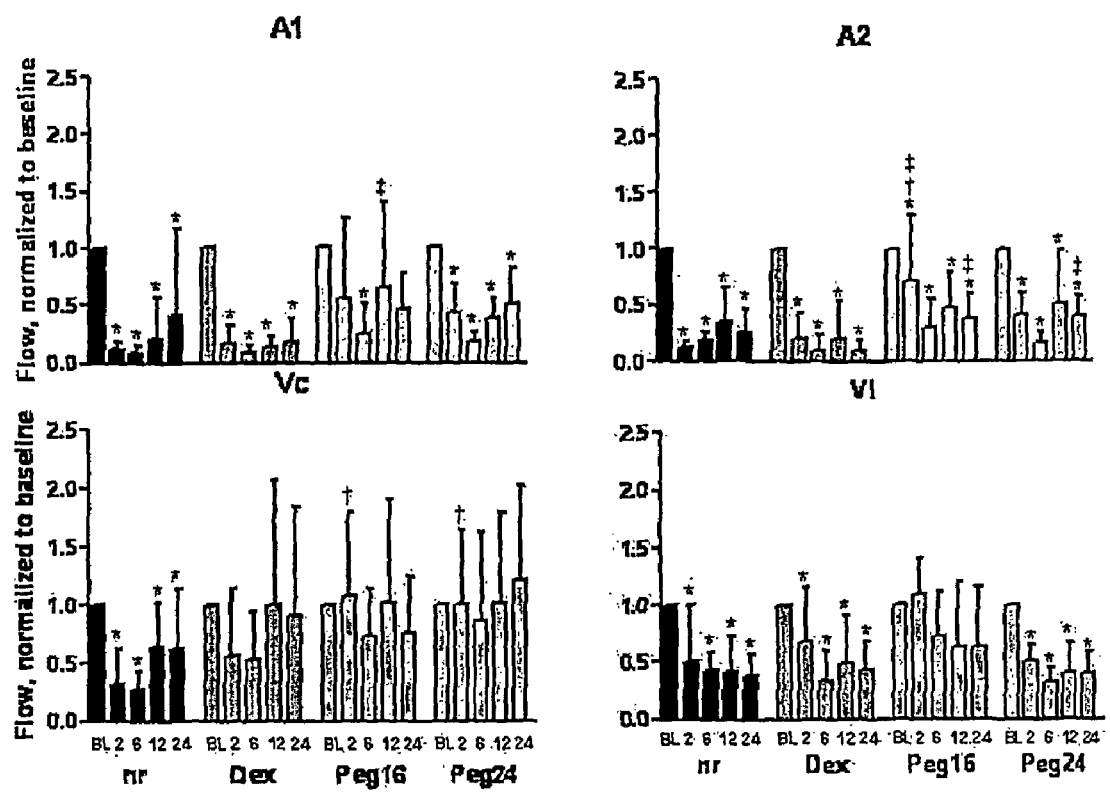
FIG. 5. Microvascular flow rate calculated for each vessel, averaged and normalized to baseline. *p<0.05 vs. baseline; †p<0.05 vs. NR group; ‡p<0.05 vs. Dex group FIG. 6. FCD for no treatment (black bars), and treatment with dextran (dark grey bars), PEG-BSA-16 (grey bars) and PEG-BSA-24 (light grey bars) at all time points. *p<0.05 vs. baseline; †p<0.05 vs. NR group; ‡p<0.05 vs. Dex group; § p<0.05 vs. PEG-BSA-16 group.

FIG. 4 shows the relative changes in RBC velocity, which were significantly reduced in all groups being statistically significantly higher for the PEG-BSA treatment groups vs. the NR and Dex groups. Changes of flow relative to baseline are shown in FIG. 5, being generally lower than baseline in most instances, and statistically different from baseline for Dex, PEG-BSA-16 and PEG-BSA-24 in Vc vessels.

Figure 6:
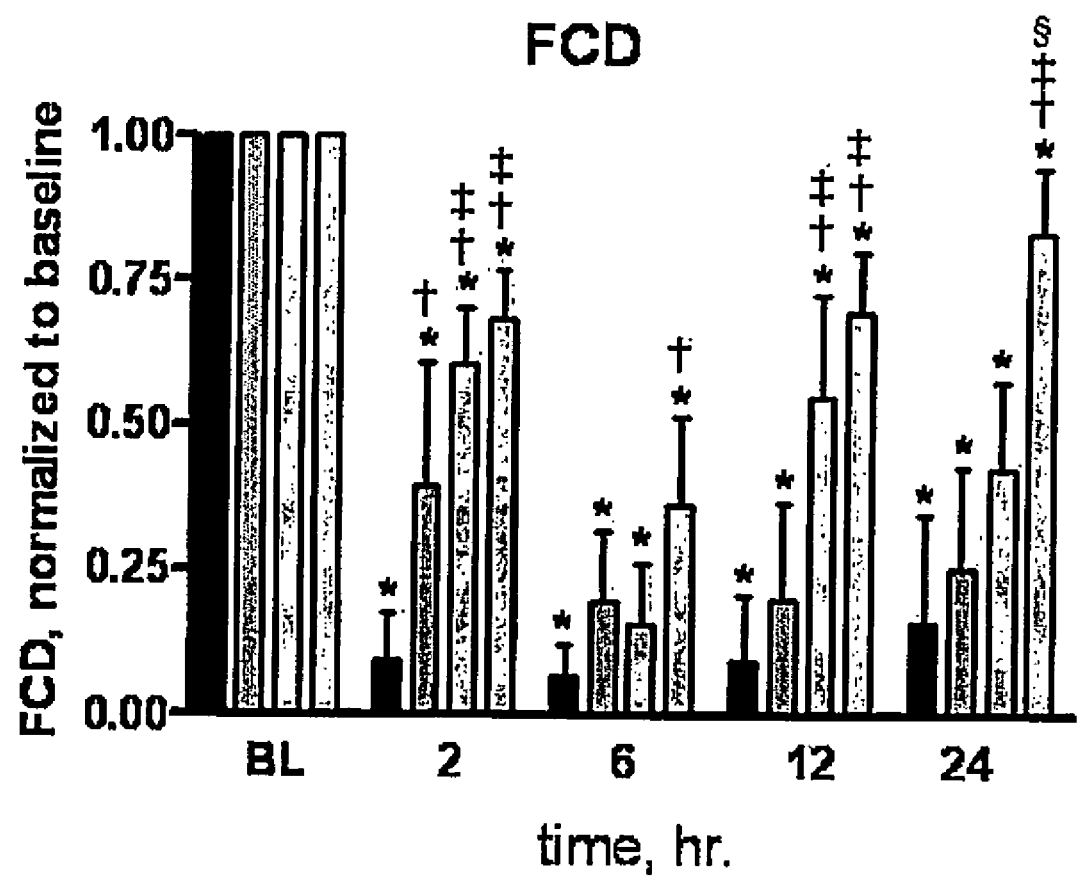

FCD was significantly below baseline for all groups and time points (FIG. 6). FCD of the PEG-BSA-24 treatment group at t=24 hr was significantly higher than at t=6 and 12 hr. FCD was at pathologically low levels for the NR group, and improved somewhat, but not statistically significantly in the Dex group. FCD showed the greatest reduction for all resuscitation groups at t=6 hr after LPS injection.

Figure 7:
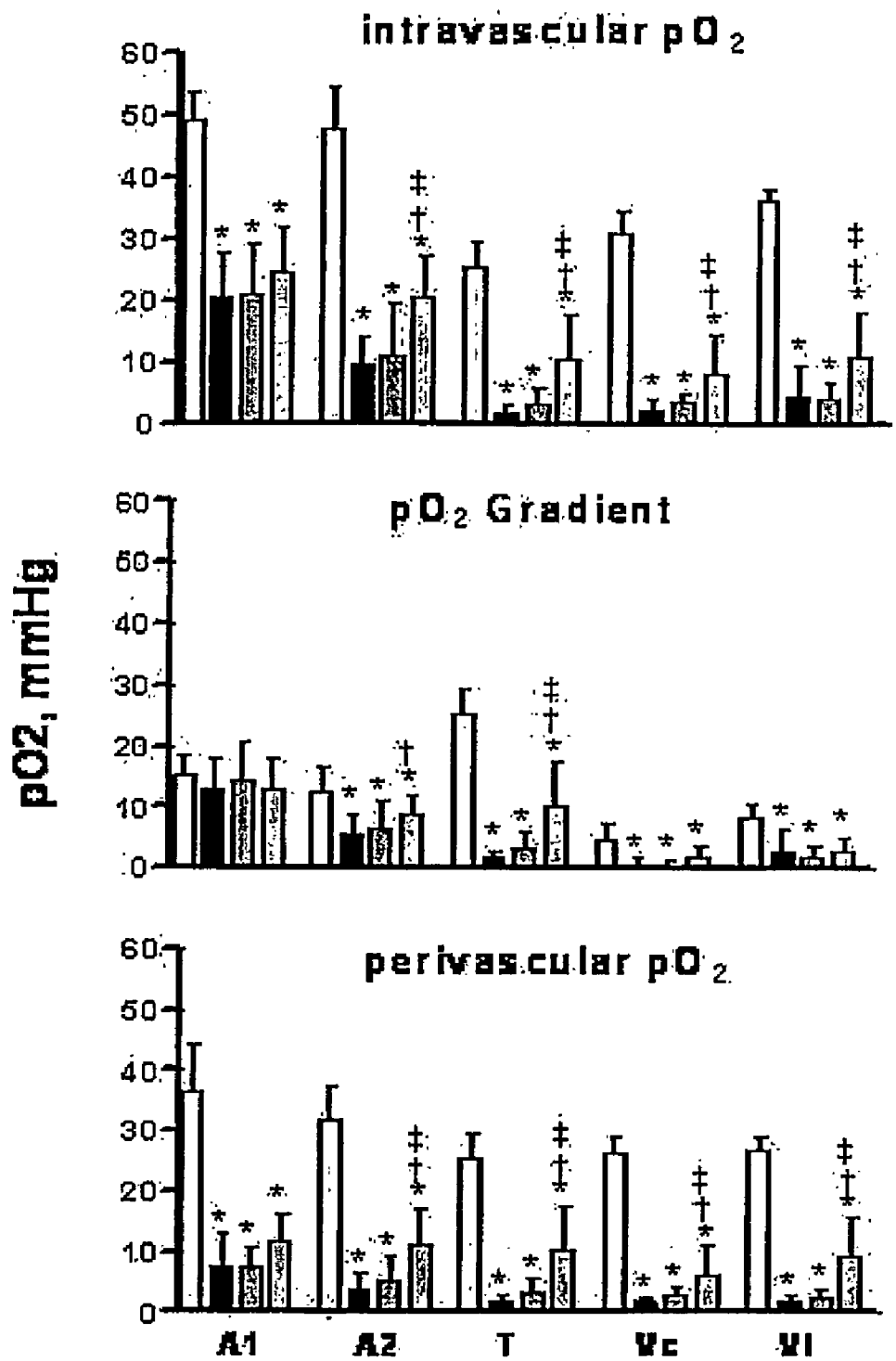
FIG. 7. Intravascular $pO_2$, vessel wall gradient, and perivascular $pO_2$ for normal control (white bars), no treatment (black bars) and treatment with dextran (dark grey bars) and PEG-BSA-24 (light grey bars) at time point t=6 hr measured in arterioles A1 and A2, the tissue T, and venules Vc and VL, at the time point t=6 hr. *p<0.05 vs. control group; †p<0.05 vs. NR group; ‡p<0.05 vs. Dex group.

Microvascular and Tissue $pO_2$. Thirteen hamsters (NR, n=4, Dex, n=4 and PEG-BSA-24, n=5) were used for $pO_2$ measurements at t=6 hr after LPS injection since this was the critical period of the septic process. Baseline systemic parameters (MAP, HR, blood gasses and microcirculatory parameters (Table 2) were the same as those previously studied (Table 1). FIG. 7 shows the $pO_2$ distribution in the 3 groups and in a control group of normal hamsters. Vessel wall gradients, i.e., the difference between intraluminal $pO_2$ and the perivascular $pO_2$ are also shown in FIG. 7. PEG-BSA-24 treatment group had the highest intravascular $pO_2$ when compared to the other treatment groups. The vessel wall $O_2$ gradient in the endotoxemia groups was not different from the control group in A1 vessels, while it was significantly lower in other vessel orders. Perivascular $pO_2$ was significantly higher in PEG-BSA-24 treatment group (except in A1 vessels) vs. the remainder of treatment groups and was consistently lower than control.

Oxygen Release to the Tissue. Calculations of oxygen delivery by the microcirculation are shown in Table 3 using data from the largest entrance and exit vessel, namely A1 and V1 vessels. Oxygen release for Dex and PEG-BSA-24 is approximately the same. Significant differences in oxygen release are evident using data from A2 and Vc vessels.

Figure 8:
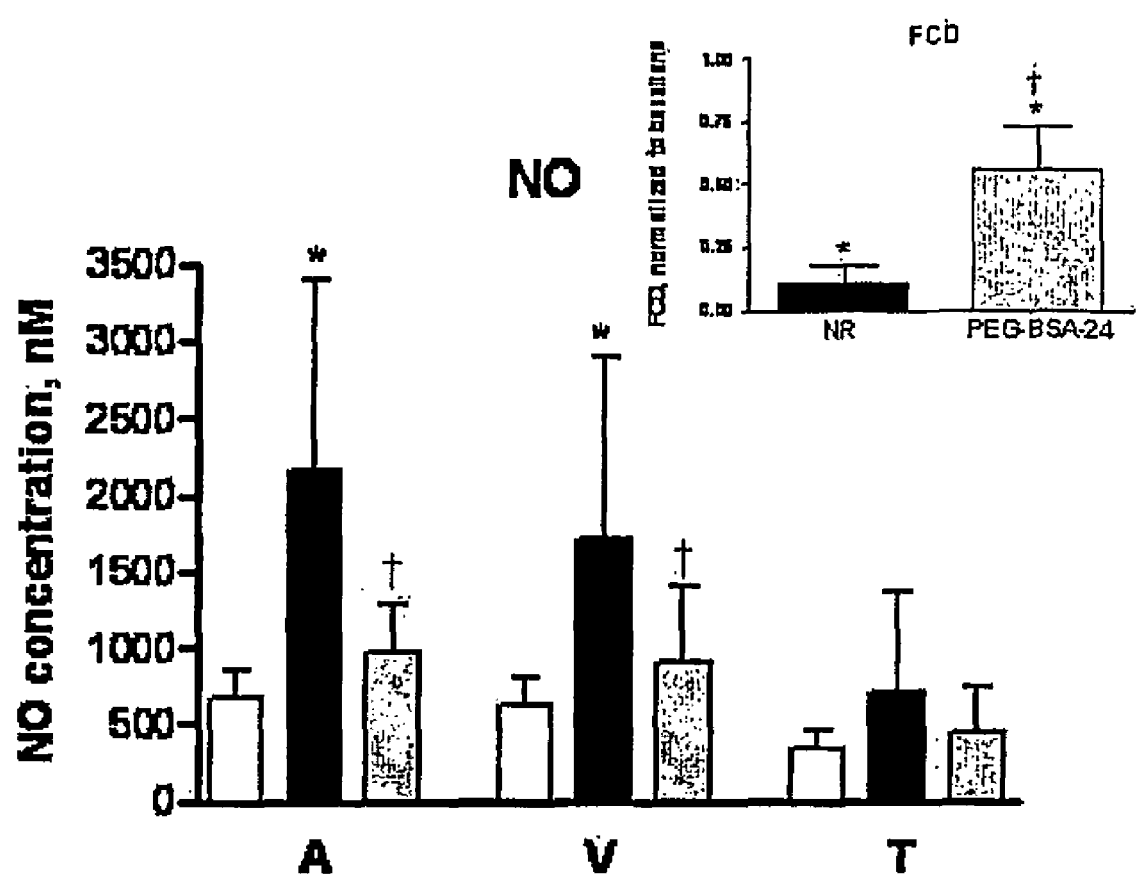
FIG. 8. Perivascular NO concentration for normal control (white bars), no treatment (black bars) and treatment PEG-BSA-24 (grey bars) at time point t=6 hr measured near arterioles A, venules V, and the tissue T. p<0.05 vs. Control; p<0.05 vs. NR group. FCD measured in this group and time point shown in small window. *p<0.05 vs. control group; †p<0.05 vs. NR group.

Perivascular NO Concentration. Perivascular NO concentration at t=6 hr (FIG. 8) in control hamsters was: arterioles (A), 670±183 nM; tissues (T), 336±112 nM; and venules (V), 624±174 nM, which was obtained from normal hamsters. NO concentrations, obtained in 7 preparations, were for NR group (n=4); A 2,152±1,237 nM (n=11); T, 696±668 nM (n=9); and, V, 1,713±1,185 nM (n=14), which in arterioles and venules was significantly higher than in the control animals. NO concentration in the PEG-BSA-24 group (n=3) was: A, 962±318 nM (n=10); T, 446±292 nM (n=5); and, V, 904±501 nM (n=9), which was significantly lower than in the NR group, but not significantly different from control.

Figure 9:
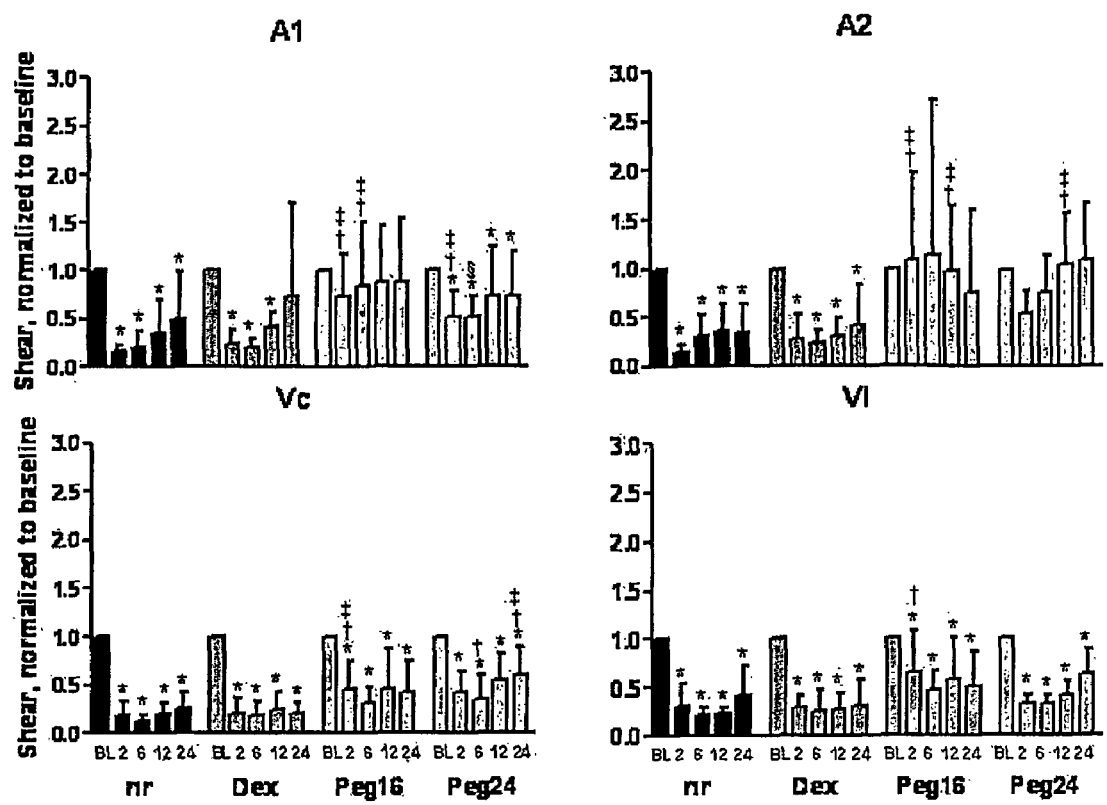
FIG. 9. Shear rate calculated from the data in FIGS. 3 & 4. Absolute values of shear rate at baseline are as follows: NR group: A1, 731±330 sec−1, A2, 1,028±274 sec−1, Vc, 504±311 sec−1, V1, 201±79 sec−1; Dex group: A1, 981±412 sec−1, A2, 1,153±542 sec−1, Vc, 375±112 sec−1, V1, 228±107 sec−1; PEG-BSA-16 group: A1, 722±392 sec−1, A2, 1,133±492.7 sec−1, Vc, 4056±196 sec−1, V1, 186±65 sec−1: PEG-BSA-24 group: A1, 999±390 sec−1, A2, 1,201±381 sec−1, Vc, 675±491 sec−1, V1, 267±112 sec−1. *p<0.05 vs. baseline; †p<0.05 vs. NR group; ‡p<0.05 vs. Dex group; § p<0.05 vs. PEG-BSA-16 group.

Shear Rate in the Microcirculation. Values of shear rate for each time point, vessel type and treatment group are shown in FIG. 9. LPS induced endotoxemia reduced shear rate in all vessel order observed. Dex treatment could not maintain shear rate. Both PEG-BSA treatment could maintain shear rate in the arterioles but not in venules.

TABLE 1

| Systemic Parameters, LPS-L and LPS-H groups | | | | | | |
|---|---|---|---|---|---|---|
| | Baseline | 1 hr. | 2 hr. | 6 hr. | 12 hr. | 24 hr. |
| MAP, mmHg | | | | | | |
| LPS-L | 120.4 ± 12.6 | 114.6 ± 13.8 | 130.1 ± 13.8 | 110.9 ± 16.9 | 110.8 ± 9.5 | 108.6 ± 26.3 |
| LPS-H | 116.2 ± 11.4 | 115.4 ± 13.5 | 127.3 ± 13.6 | 92.7 ± 5.7[a] | 86.0 ± 22.7[a] | 99.6 ± 13.3 |
| HR, bpm | | | | | | |
| LPS-L | 393.9 ± 49.0 | 412.2 ± 65.3 | 450.8 ± 39.8 | 448.1 ± 47.1 | 407.0 ± 73.6 | 424.9 ± 73.8 |
| LPS-H | 405.0 ± 36.5 | 413.5 ± 44.8 | 443.2 ± 33.5 | 362.3 ± 51.9 | 405.1 ± 52.5 | 368.8 ± 64.5 |

TABLE 1-continued

Systemic Parameters, LPS-L and LPS-H groups

| | Baseline | 1 hr. | 2 hr. | 6 hr. | 12 hr. | 24 hr. |
|---|---|---|---|---|---|---|
| Hct, % | | | | | | |
| LPS-L | 46.0 ± 1.0 | | | | | |
| LPS-H | 46.8 ± 2.2 | 42.5 ± 2.1 | | | | 39.0 ± 0.8 |
| Hb, g/dl | | | | | | |
| LPS-L | 14.4 ± 1.1 | | | | | |
| LPS-H | 14.3 ± 1.3 | 13.0 ± 1.8 | | | | 12.0 ± 1.3 |

MAP, mean arterial blood pressure;
HR, heart rate;
Hct, systemic hematocrit;
Hb, hemoglobin concentration.
[a] $P < 0.05$ relative to baseline

TABLE 2

Systemic Parameters, Resuscitation group

| | Baseline | 1 hr. | 2 hr. | 6 hr. | 12 hr. | 24 hr. |
|---|---|---|---|---|---|---|
| MAP, mmHg | | | | | | |
| NR | 116.2 ± 11.4 | 115.4 ± 13.5 | 127.3 ± 13.6 | 92.7 ± 5.7[a] | 6.0 ± 22.7[a] | 99.6 ± 13.3 |
| Dex | 123.4 ± 2.4 | 25.9 ± 7.8 | 130.4 ± 12.5 | 110.9 ± 11.4 | 14.4 ± 5.1 | 112.7 ± 3.9 |
| PEG-BSA-16 | 126.2 ± 9.6 | 128.2 ± 7.1 | 140.4 ± 8.0 | 115.6 ± 8.6 | 116.8 ± 10.0 | 110.6 ± 17.0 |
| PEG-BSA-24 | 115.1 ± 9.4 | 128.2 ± 9.2 | 132.9 ± 2.8 | 111.5 ± 14.1 | 113.9 ± 7.7 | 105.2 ± 11.2 |
| HR, bpm | | | | | | |
| NR | 405.0 ± 36.5 | 413.5 ± 44.8 | 443.2 ± 33.5 | 362.3 ± 51.9 | 405.1 ± 52.5 | 368.8 ± 64.5 |
| Dex | 385.3 ± 37.0 | 378.4 ± 3.3 | 443.5 ± 67.1 | 441.3 ± 3.3 | 376.8 ± 44.9 | 398.0 ± 36.9 |
| PEG-BSA-16 | 411.4 ± 43.3 | 437.8 ± 37.0 | 458.2 ± 18.1 | 426.1 ± 56.4 | 425.7 ± 58.7 | 413.0 ± 61.2 |
| PEG-BSA-24 | 416.1 ± 32.4 | 399.8 ± 62.4 | 412.3 ± 30.4 | 414.4 ± 76.1 | 487.4 ± 14.4 | 428.3 ± 66.2 |
| Hct, % | | | | | | |
| NR | 46.8 ± 2.2 | 42.5 ± 2.1 | | | | 39.0 ± 0.8 |
| Dex | | | | | | |
| PEG-BSA-16 | 46.5 ± 1.9 | | 43.0 ± 2.7 | 43.8 ± 2.2 | 42.5 ± 3.7 | 41.8 ± 1.7 |
| PEG-BSA-24 | 46.5 ± 1.7 | | 44.7 ± 0.6 | 46.0 ± 1.7 | 45.5 ± 3.6 | 42.5 ± 0.7 |
| Hb, g/dl | | | | | | |
| NR | 14.3 ± 1.3 | 13.0 ± 1.8 | | | | 12.0 ± 1.3 |
| Dex | | | | | | |
| PEG-BSA-16 | 14.1 ± 0.6 | | 13.5 ± 0.7 | 14.2 ± 0.5 | 13.5 ± 2.0 | 12.8 ± 0.1 |
| PEG-BSA-24 | 14.5 ± 0.8 | | 14.0 ± 0.5 | 14.5 ± 1.1 | 14.5 ± 0.5 | 13.4 ± 0.4 |

MAP, mean arterial blood pressure;
HR, heart rate;
Hct, systemic hematocrit;
Hb, hemoglobin concentration;
NR, no resuscitation;
Dex, Dextran 70;
PEG-BSA-16, PEG-BSA 16 ml/kg/hr;
PEG-BSA-24, PEG-BSA 24 ml/kg/hr.
[a] $P < 0.05$ relative to baseline

TABLE 3

Systemic Parameters, at t = 6 hr for $pO_2$ and NO concentration measurement

| | Baseline | 6 hr. |
|---|---|---|
| MAP, mmHg | | |
| NR | 111.1 ± 13.7 | 94.3 ± 15.7[a] |
| Dex | 114.6 ± 19.2 | 116.7 ± 3.8 |
| PEG-BSA-24 | 108.5 ± 10.2 | 103.7 ± 14.0 |
| HR, bpm | | |
| NR | 393.4 ± 50.9 | 431.9 ± 37.8 |
| Dex | 420.8 ± 42.9 | 473.0 ± 50.8 |
| PEG-BSA-24 | 443.7 ± 38.8 | 452.9 ± 56.9 |
| Hct, % | | |
| NR | 45.5 ± 0.8 | 45.9 ± 1.8 |
| Dex | 45.0 ± 1.0 | 44.0 ± 1.7 |
| PEG-BSA-24 | 46.5 ± 0.9 | 43.6 ± 1.8[a] |
| Hb, g/dl | | |
| NR | 13.3 ± 0.6 | 13.7 ± 1.4 |
| Dex | 12.9 ± 0.4 | 13.3 ± 1.2 |
| PEG-BSA-24 | 13.4 ± 0.9 | 13.2 ± 0.7 |

TABLE 3-continued

Systemic Parameters, at t = 6 hr
for pO$_2$ and NO concentration measurement

|  | Baseline | 6 hr. |
|---|---|---|
| Whole blood viscosity, cp |  |  |
| NR |  | 3.04 ± 0.16 |
| Dex |  | 3.34 ± 0.41 |
| PEG-BSA-24 |  | 3.21 ± 0.7 |
| Plasma viscosity, cp |  |  |
| NR |  | 1.10 ± 0.07 |
| Dex |  | 1.24 ± 0.01 |
| PEG-BSA-24 |  | 1.30 ± 0.07 |
| COP, mmHg |  |  |
| NR |  | 14.2 ± 1.5 |
| Dex |  | 16.4 ± 1.0 |
| PEG-BSA-24 |  | 19.4 ± 3.2 |
| pH |  |  |
| NR | 7.36 ± 0.02 | 7.40 ± 0.04 |
| Dex | 7.37 ± 0.04 | 7.41 ± 0.04 |
| PEG-BSA-24 | 7.36 ± 0.01 | 7.42 ± 0.04 |
| paO2, torr |  |  |
| NR | 59 ± 1 | 81 ± 17 |
| Dex | 56 ± 5 | 74 ± 5 |
| PEG-BSA-24 | 63 ± 5 | 75 ± 13 |
| paCO2, torr |  |  |
| NR | 56 ± 5 | 40 ± 4 |
| Dex | 55 ± 7 | 38 ± 6 |
| PEG-BSA-24 | 54 ± 5 | 36 ± 3 |
| BE, mmmol/L |  |  |
| NR | 5.5 ± 2.0 | −1.0 ± 1.5 |
| Dex | 5.4 ± 2.7 | −1.2 ± 3.0 |
| PEG-BSA-24 | 4.4 ± 2.1 | −1.3 ± 2.3 |

MAP, mean arterial blood pressure; HR, heart rate; Hct, systemic hematocrit; Hb, hemoglobin concentration; COP, colloid osmotic pressure; NR, no resuscitation; Dex, Dextran 70; Peg 16, PEG-BSA 16 ml/kg/hr; PEG-BSA-24, PEG-BSA 24 ml/kg/hr.
[a]P < 0.05 relative to baseline

TABLE 4

Comparison of oxygen release among control, NR, Dex and PEG-BSA-24

|  | Control | NR | Dex | PEG-BSA-24 |
|---|---|---|---|---|
| A1-V1 | 24 (1) | 6.4 (0.26) | 10.8 (0.45) | 11.2 (0.47) |
| A2-Vc | 24 (1) | 0.43 (0.02) | 1.5 (0.06) | 14.1 (0.59) |

Oxygen release = ΔSat O$_2$ × Flow; ( ), normalized to control; NR, no resuscitation; Dex, Dextran 70; PEG-BSA-24, PEG-BSA 24 ml/kg/hr.

IV. Discussion

The principal finding of this study is that fluid treatment of endotoxemia with PEG-BSA maintains/restores impaired microvascular function increasing FCD and tissue pO$_2$ to near normal levels, a result not obtained with an identical treatment using Dextran 70 kDa. These effects were obtained in a model of endotoxemia that although not lethal, caused a significant reduction of FCD which persisted up to 24 hours in the absence of treatment, at which time FCD was less than 20% of baseline. Endotoxemia caused a significant increase in perivascular NO in arterioles and venules, which was reduced by the increased perfusion due to treatment with PEG-BSA-24. There was a significant decrease of perivascular tissue pO$_2$ at all time points, which was in part corrected by treatment with PEG-BSA-24.

FCD was reduced to 7% of baseline at t=6 hr in the LPS-H group, recovering only to 16% at t=24 hr, a condition of persistent illness. FCD was reduced to 30% of baseline at t=6 hr in the LPS-L group, recovering to 69% at t=24 hr. This disparity of outcome led to the selection of LPS-H dosage to study the effects of different resuscitation fluids, which was twice the dosage used by Hoffman et al. who used 2 mg/kg of LPS from *E. coli*, serotype 0128:B12 for golden Syrian hamster to produce normotensive sepsis (6).

In the present model a significant impairment of microvascular function occurred 6 hr after LPS administration (FIG. 2). Since this time point corresponded to the greatest impairment of microvascular function for all treatments modalities, it was used to characterize the effect of treatment on perivascular NO concentration and intravascular pO$_2$. This choice was due to practical considerations regarding limitations of the use of animal subjects, since each measurement of NO and pO$_2$ at each time point requires two independent groups of animals.

Microvascular hemodynamic changes in sepsis. A common denominator of most studies of microvascular effects of endotoxemia is the decrease of tissue perfusion, although the mechanism responsible for this is not clear since the decrease of blood pressure, vasodilatation and constriction, and loss of blood volume coexist (2, 25). The principal microvascular finding is the observation of increased venular leakage (26, 27). Dilatation of arterioles in skeletal muscle was reported by Cryer et al. (28) due to *E. coli* induced sepsis. A rat skeletal muscle model of sepsis showed that microvascular perfusion was impaired due to the decrease in FCD in the absence of hypotension (29).

During endotoxemia blood flow has been reported to cease completely in the smaller arterioles although it is maintained in larger microvessels bypassing the capillary circulation due to vasoconstriction and RBC aggregation (30). Increased accumulation of neutrophils (31) and increased platelet aggregation and leukocyte plugging consequent to the decrease of perfusion pressure occur as soon as perfusion pressure is decreased. In normotensive septic shock, peripheral blood flow is reduced (32). Severe sepsis and septic shock cause hemodynamic alterations characterized by lower RBC velocity, A-V shunting, decreased RBC deformability, RBC aggregation, vascular leaks and venous pooling (7, 33, 34, 35, 36, 37), lowered RBC deformability (38, 39, 40) and tissue edema resulting from vascular leakage and capillary plugging contribute to the decrease in FCD.

Fluid therapy is an essential component in the treatment of sepsis and presumably reverses microvascular deficits. Previous experimental and clinical studies of sepsis and/or septic shock (6, 7, 41, 42, 43, 44, 45, 46, 47, 48, 49) focused on maintaining circulatory volume with low viscosity plasma expanders such as hypertonic saline, dextran, gelatin, HES and albumin, without reaching conclusive results.

The present endotoxemia model showed vasoconstriction in arterioles and vasodilation in venules after LPS injection which lasted throughout the study. Venules had stopped flow, RBC aggregation and plugging. This was different from the usual finding of vasodilation associated with sepsis, but congruent with the observation that in the present model sepsis results in the impairment of microvascular perfusion. FCD was impaired within 2 hours after LPS injection and reached its lowest point 6 hours after injection. A similar result was found in the study of Mcdonald et al., who reported that myocardial function was impaired 5-6 hr after injection of LPS (50). Friesenecker et al. and Tsai et al., also showed that vasoconstriction lowers FCD, in the chamber window model (23, 51).

Dextran and PEG-BSA resuscitation significantly increased MAP relative to the no resuscitation group. Dextran appeared to maintain circulatory volume as evidenced by the lack of significant changes in Hct, but did not improve FCD. Conversely the PEG-BSA-24 group continuously improved FCD to the extent that it was not statistically different from baseline at the end of the observation period, while Dex improved FCD at t=2 hr, but not after t=6 hr. Dex maintained systemic and microvascular conditions, however microvascular effects were short lived since microvascular flow only returned to normal in Vc venules at t=12 & 24 hr. These effects are probably due to the short serum half life of Dextran 70 (~6 hr in normal tissue and conditions). The finding that Hct of the PEG-BSA-24 group was significantly lower than baseline at t=6 hr (Table 2), while the Hct was the same for the dextran group is indicative that blood volume was increased in the PEG-BSA group, an effect attributable to decreased extravasation due to its larger molecular dimensions and therefore longer lasting oncotic effects. Furthermore, the PEG-BSA-24 group had better FCD when compared with PEG-BSA-16 ($p<0.05$, at t=24 hr) indicating microvascular function recovery is aided by the improved fluid retention.

Assaly et al. used PEG-HSA (human serum albumin) to maintain systemic circulation in sepsis with both LPS injection and in the CLP (Cecum ligate pucture) septic shock models (52). Their study showed that extravasation of HSA is reduced by PEGylation. The PEG HSA conjugation used in that study had a molecular mass of 94 kDa, carrying an average six copies of PEG, whereas the PEG used in the present study is about 130 kDa presumably leading to a larger molecule and a lesser tendency to extravasate.

Microvascular $pO_2$ Distribution in Sepsis. Intravascular and tissue $pO_2$ were significantly reduced from normal levels throughout the observation period. However, treatment with PEG-BSA-24 yielded significantly higher $pO_2$ values (FIG. 7). The vessel wall oxygen gradient was decreased in animals with sepsis. Previous findings show that microvascular oxygen gradients increase in vasoconstriction, and vice versa (23). In the present study, although arterioles vasoconstricted and venules vasodilated, the vessel oxygen gradients decreased relative to control in both vessel type. This suggests that smooth muscle or/and endothelial cells oxygen consumption was decreased.

Dex and PEG-BSA-24 released oxygen to the tissue (Table 3) at approximately the same rate on the basis of data from A1 and V1 vessels. However, data from A2 and Vc vessel shows a major difference between groups. This discrepancy may be explained by shunting in vessels at higher branching levels than those tested in this study (53) since larger vessels may deliver and collect oxygen from different tissues.

Ellis et al. (10) measured oxygen saturation in the capillaries in rat skeletal muscle during sepsis showing that tissue oxygen extraction ratio was impaired because of maldistribution of oxygen delivery. In the present study tissue and collecting venule $pO_2$ were the same for no treatment and treatment groups. Thus, changes in tissue $pO_2$ do not appear to be due to differences in tissue oxygen consumption but rather collecting venules $pO_2$, which is in part determined by arteriolar-venular blood shunting.

The finding that vasoconstriction was prevalent in this tissue is counterintuitive because the prevalent hypoxia in both untreated and treated animals should lead to vasodilatation. This result may be linked to the elevated levels of NO found in the tissue.

Tissue NO Concentration in Sepsis. Activation of iNOS production by endotoxin is well established, and albumin based fluid resuscitation is reported to decrease NOS II expression in a rat sepsis model (49). In the present study NO concentration was measured at t=6 hr after LPS injection, which corresponds to the time at which Walley et al. (49), measured the highest NOS II expression in the rat, and Bateman et al., (54) showed that high NO concentrations in plasma lowered RBC deformability and capillary density.

According to Colasanti and Suzuki, physiological low levels of NO may exert beneficial effects, while high levels lead to cytotoxic effects (55) suggesting that selective iNOS inhibition is beneficial in sepsis, while non-selective NOS inhibition is detrimental. Feihl et al. (56), proposed that the effects of NO that serve to promote homeostasis occur at low (nanomolar) NO concentrations. In the present study perivascular NO concentration in the NR group averages 2,150 nM in arterioles and 1,710 nM in venules. Considering that FCD was impaired in the present sepsis model while NO concentration was in the milimolar range suggests that these factors are related. In the present study PEG-BSA-24 improved FCD and decreased perivascular NO to normal concentrations.

The present results show that maintenance of fluid volume or its expansion by the introduction of PEG-BSA is associated with a vasodilatory effect at the level of arterioles, related to the restoration of microvascular shear rate to near normal levels (FIG. 9), a requirement for the production of endothelial dependant vasodilators such as NO, prostacyclin and endothelin (the latter dependant on dosage and stimulus). Shear stress was not determined due to the need to restrict blood samples did not allow a determination of blood and plasma viscosity at different time points. However, since there were no significant differences in plasma viscosity, the calculated shear rate should be representative of shear stress at the microvascular wall. It is notable that PEG-BSA treatment normalized shear rate in arteriolar microcirculation, which is the region maximally affected by vasoconstriction.

The present results show that increased FCD and flow decreases tissue NO concentration to near normal levels in sepsis. There is some evidence that albumin reacts with NO (57); however, the increase of albumin due to the PEG-Alb treatment is about 15% above baseline, which would seem unlikely to account for the observed decrease in NO. It is likely that the significantly increased FCD distributes RBC hemoglobin more uniformly in the tissue facilitating scavenging of NO, therefore the effects due to PEG-BSA should be due to improved perfusion.

In conclusion, the present study shows that PEG-BSA fluid therapy significantly improves microvascular recovery in the treatment of endotoxemia through the restoration of FCD. Recovery of FCD appears to be a multifactorial process that involves the improvement of flow, possibly the increase in capillary pressure, improvement of perivascular and tissue oxygen tension, normalization of shear rate and the decrease in perivascular NO concentration. These events should be in part due to improved fluid retention in the circulation by the larger molecular dimension of PEG-BSA, reduced edema, and the reduction of RBC aggregation and improvement of RBC flexibility, although this was not tested in the present study. Normalization of microvascular function may also be due to the reduction of iNOS. Improved flow and FCD was directly related to the increase of tissue $pO_2$ and could be related to facilitated NO scavenging by blood hemoglobin thus normalizing NO concentration. The beneficial effects at the level of the microcirculation derived from PEG-BSA treatment are already present at the critical time point t=6 hr after LPS infusion; however, at this time point there is essentially no difference in systemic parameters between treatment with Dex, PEG-BSA and no treatment. Thus, early treatment of microvascular malfunction may be a requirement for insuring recovery and may improve survival of sepsis patients.

In summary, this aspect of the present invention deals with the treatment of sepsis and endotoxemia. This is usually managed according to the "VIP" principles, namely Ventilate, Infuse and Pump based on the concepts that: 1) it is essential to maintain adequate tissue oxygenation; 2) administration of fluid is required to treat hypotension and maintain adequate tissue perfusion; and, 3) central blood pressure should be maintained by means of vasopressor and/or inotropic agents in order to further support tissue perfusion restoration following fluid resuscitation. These principles which guide the management of septic shock lead to treatment modalities that principally address systemic conditions. However, correction of central deficits does not necessarily treat the problem at the microscopic functional level thus leading to uncertain results as shown by the continued high morbidity and mortality associated with severe sepsis (3).

The finding that maintenance of FCD is critical for insuring survival during shock led to the invention that PEG-Albumin, proven effective to treat shock, would be effective in treating sepsis, through the same mechanism, namely the recovery of FCD. This parameter is compromised in sepsis due to the compression of the capillaries by tissue edema, endothelial swelling and plugging by leukocytes or red blood cells whose rigidity is increased as a consequence of endotoxemia. Maintenance or restoration of FCD should be significant in the treatment of endotoxemia since a key component of treatment is the eradication of pathogens, an effect that is fully dependant on the delivery of antimicrobial agents through the circulation, which is compromised and ineffectual as FCD decreases.

Experimental findings in the hamster window model subjected to endotoxemia by the injection of LPS and resuscitated with PEG-Albumin determined that this material maintains andrestores impaired microvascular function by increasing FCD and tissue $pO_2$ to near normal levels, while lowering perivascular NO concentration when compared to an identical treatment using a conventional colloidal plasma expander such as dextran 70 kDa.

According to the present invention PEG-Albumin fluid therapy provides significantly improved microvascular recovery in the treatment of endotoxemia through mechanisms related to the restoration of FCD. Recovery of FCD is a multi factorial process involving the improvement of flow, the increase in capillary pressure, improvement of perivascular and tissue oxygen tension, normalization of shear rate and the decrease in perivascular NO concentration. These events are in part due to improved fluid retention in the circulation by the larger molecular dimension of PEG-Albumin, reduced edema, reduced RBC aggregation and improved RBC flexibility. A consequence of this is improved flow, which increases tissue oxygen $pO_2$. Furthermore, increased FCD and flow allows blood hemoglobin to augment NO scavenging thus normalizing NO concentration. The beneficial effects at the level of the micro-circulation derived from PEG-Albumin treatment are already present at the critical time point t=6 hr after LPS infusion; however, at this time point there is essentially no difference in systemic parameters between treatment with dextran, PEG-Albumin and no treatment. Thus early treatment of micro-vascular malfunction is required for insuring recovery and improves survival of sepsis patients.

The essence of this aspect of the invention is that PEG-Albumin is effective in opening closed capillaries. Sepsis causes the closure of capillaries, and PEG albumin is able to open capillaries closed by sepsis, thus allowing the therapeutic intervention to reach the tissue.

REFERENCES

1. Weil M H and Shubin H: The "VIP" approach to the bedside management of shock. *JAMA* 1969; 207:337-340.
2. Vincent J-L, Bruzzi de Carvalho F and Backer DD: Management of septic shock. *Ann Med* 2002; 34:606-613.
3. Alberti C, Brun-Buissson C, Goodman S V, et al.: Influence of systemic inflammatory response syndrome and sepsis on outcome of critically ill infected patients. *Am J Respir Grit Care Med* 2003; 168:77-84.
4. Kerger H, Saltzman D J, Menger M D, et al.: Systemic and subcutaneous microvascular $pO_2$ dissociation during 4-h hemorrhagic shock in conscious hamsters. *Am J Physiol* 1996; 270:H827-H836.
5. Nevière R and Sibbald W: Microvascular alterations in sepsis. *Sepsis* 2000; 4:81-88.
6. Hoffmann J N, Volner B, Laschke M W, et al.: Hydroxyethyl starch (130 kD), but not crystalloid volume support, improves microcirculation during normotensive endotoxemia. *Anesthesiology* 2002; 97:460-470.
7. Morisaki H, Bloos F, Keys J, et al. Compared with crystalloid, colloid therapy slows progression of extrapulmonary tissue injury in septic sheep. *J Appl Physiol* 1994 77:1507-18.
8. Arming P B, Sair M, Winlove C P, et al.: Abnormal tissue oxygenation and cardiovascular changes in endotoxemia. *Am J Res Crit Care Med* 1999; 159:1710-1715.
9. Sair M, Ethaerington P J, Curzen N P, et al.: Tissue oxygenation and perfusion in endotoxemia. *Am J Physiol* 1996; 271:H1620-H1625.
10. Ellis C G, Bateman R M, Sharpe M D, et al.: Effect of a maldistribution of microvascular blood flow on capillary $O_2$ extraction in sepsis. *Am J Physiol Heart Circ Physiol* 2002; 282:H156-H164.
11. Wettstein R, Cabrales P, Erni D, et al.: Resuscitation from hemorrhagic shock with MalPEG-albumin: Comparison with MalPEG-hemoglobin. *Shock* 2004; 22:351-357.
12. Acharya A S, Manjula B N and Smith P K, inventor. Hemoglobin crosslinkers. U.S. Pat. No. 5,585,484, 1996.
13. Intaglietta M and Tompkins W R: Microvascular measurements by video image shearing and splitting. *Microvasc Res* 1973; 5:309-312.
14. Kerger H, Torres, Filho I P, et al.: Systemic and subcutaneous microvascular oxygen tension in conscious syrian golden hamsters. *Am J Physiol* 1995; 267:H802-810.
15. Kerger H, Groth G, Kalenka A et al. $pO_2$ measurements by phosphorescence quenching: characteristics and applications of an automated system. *Microvasc Res* 2003; 65:32-38.
16. Vanderkooi J M, Maniara G, Green T J et al.: An optical method for measurement of dioxygen concentration based upon quenching of phosphorescence. *J Biol Chem* 1987 262:5476-82.
17. Budai D and Molnár Z: Novel carbon fiber microelectrodes for extra cellular electrophysiology. *Acta Biologica Szegediensis* 2001; 45:65-73.
18. Sarelius I H: Cell flow path influences transit time through striated muscle capillaries. *Am J Physiol Heart Circ Physiol* 1986; 250:H899-H907.
19. Sarelius I H, Maxwell L C, Gray S D, et al.: Capillarity and fiber types in the cremaster muscle of rat and hamster. *Am J Physiol* 1983; 245:H368-H374.
20. Cabrales P, Tsai A G and Intaglietta M: Microvascular pressure and functional capillary density in extreme hemodilution with low and high plasma viscosity expanders. *Am J Physiol Heart Circ Physiol* 2004; 287:H363-H373.
21. Nase G P, Tuttle J and Bohlen H G: Reduced perivascular $pO_2$ increases nitric oxide release from endothelial cells. *Am J Physiol Heart Circ Physiol* 2003; 285:H507-15.
22. Sakai H, Tsai A G, Rohlfs R J, et al.: Microvascular responses to hemodilution with Hb vesicles as RBC substitutes: Influence of $O_2$ affinity. *Am J Physiol* 1999; 276:H553-H562.
23. Friesenecker B, Tsai A G, Dunser M W, et al.: Oxygen distribution in microcirculation after arginine vasopressin-induced arteriolar vasoconstriction. *Am J Physiol Heart Circ Physiol* 2004; 287:H1792-800.
24. Lipowslcy H H and Firrell J C: Microvascular hemodynamics during systemic hemodilution and hemoconcentration. *Am J Physiol* 1986; 250:H908-H922.
25. Hinshaw L B: Sepsis/septic shock. *Crit Care Med* 1996; 24:1072-1078.
26. de Carvalho H, Matos J A, Bouskela E, et al.: Vascular permiability increase and plasma volume loss induced by endotoxin was attenuated by hypertonic saline with or without dextran. *Shock* 1999; 12:75-80.
27. Zweifach B W and Thomas L: The relationship between the vascular manifestations of shock produced by endotoxin, trauma and hemorrhage. *J Exper Med* 1957; 106:385-401.
28. Cryer H M, Garrison R N, Kaebnick H W, et al.: Skeletal microcirculatory responses to hyperdynamic *Escherichia coli* sepsis in unanaesthetized rats. *Arch Surg* 1987; 122:86-92.
29. Lam C, Tyml K and Martin C: Microvascular perfusion is impaired in a rat model of normotensive sepsis. *J Clin Invest* 1994; 94:2077-2083.
30. Baker C H, Wilmoth F R and Sutton E T: Reduced RBC versus plasma microvascular flow due to endotoxin. *Circ Shock* 1986; 20:127-139.
31. Schmid-Schönbein G W: Granulocyte activation and capillary obstruction. In: D. W. Liepsich(Eds.). Blood low in large arteries: applications to atherogenesis and clinical medicine. Basel, Karger, 1990, pp. 150-159.
32. Astiz M E, Tilly E, Rackow E D, et al.: Peripheral vascular tone in sepsis. *Chest* 1991; 99:1072-1075.
33. Baskurt O K, Temiz A and Meiselman H J: Red blood cell aggregation in experimental sepsis. *J Lab Clin Med* 1997; 130:183-190.
34. Baris C, Guest M M and Frazer M E: Direct effects of endotoxin on the microcirculation. *Advances in Shock Research* 1980; 4:13-16.
35. Durocher J R, Weir M S, Lundblad E G, et al.: Effect of oral contraceptive and pregnancy on erythrocyte deformability and surface charge. *Proc Soc Exp Biol Med* 1975; 150:368-370.
36. Eichelbronner O, Sielenkamper A, Cepinskas G, et al.: Endotoxin promotes adhesion of human erythrocytes to human vascular endothelial cells under conditions of flow. *Crit Care Med* 2000; 28:1865-1870.
37. Rogers M E, Williams D T, Niththyananthan R, et al.: Decrease in erythrocyte glycophorin sialic acid content is associated with increased erythrocyte aggregation in human diabetes. *Clin Sci* 1992; 82:309-313.
38. Powell R J, Machiendo G W, Rush B F J, et al.: Effect on red cell deformability and survival in sepsis. *Curr Surg* 1989; 46:380-382.
39. Powell R J, Machiendo G W, Rush B F J, et al.: Oxygen free radicals: effect of alpha-tocopherol on red cell deformability in sepsis. *Crit Care Med* 1991; 19:732-735.
40. Uyesaka N, Hasegaewa S, Ishioka N, et al.: Effects of super-oxide anions on red cell deformability and membrane proteins. *Biorheol* 1992; 29:217-229.
41. Asfar P, Kerkeni N, Labadie F, et al.: Assessment of hemodynamic and gastric mucosal acidodid with modified fluid versus 6% hydroxyethyl satrach: a prospective, randomized study. *Int Care Med* 2000; 26:
42. Baum T D, Wang H, Rothschild H R, et al.: Mesenteric oxygen metabolism, ileal mucosal hydrogen ion concentration, and tissue edema after crystalloid resuscitation in porcine endotoxic shock: comparison of Ringer's Lactate and 6% Hetastarch. *Circulatory Shock* 1990; 30:385-397.
43. Forrest D M, Baigorri F, Chittock D R, et al.: Volume expansion using pentastarch does not change gastric-arterial $CO_2$ gradient or gastric intramucosal pH in patients who have sepsis syndrome. *Crit Care Med* 2000; 28:2254-2258.
44. Kreimeier U, Frey L, Dentz J, et al. Hypertonic saline dextran resuscitation during the initial phase of acute endotoxemia: Effect on regional blood flow. *Crit Care Med* 1991 19:801-9.
45. Marx G, Cobas Meyer M, Schuerholz T, et al.: Hydroxyethyl starch and modified fluid gelatin maintain plasma volume in a porcine model of septic shock with capillary leakage. *Int Care Med* 2002; 28:629-635.
46. Oi Y, Aneman A, Svensson M, et al.: Hypertonic saline-dextran improves intestinal perfusion and survival in porcine endotoxin shock. *Crit Care Med* 2000; 28:2843-2850.
47. Oliveira R P, Velasco I, Soriano F G, et al.: Clinical review: Hypertonic saline resuscitation in sepsis. *Critical Care* 2002; 6:418-423.
48. Shortgen F, Lacherade J, Bruneel F, et al.: Effects of hydroxyethylstarch and gelatin on renal function in severe sepsis: a multicentre randomised study. *Lancet* 2001; 357:911-916.
49. Walley K R, McDonald T E, Wang Y, et al.: Albumin resuscitation increases cardiomyocyte contractility and decreases nitric oxide synthase II expression in rat endotoxemia. *Crit Care Med* 2003; 31:187-194.
50. McDonald T E, Grinman M N, Carthy A M, et al.: Endotoxin infusion in rats induces apoptotic and survival pathways in hearts. *Am J Physiol* 2000; 279:H2053-H2061.
51. Tsai A G, Cabrales P, Winslow R M, et al.: Microvascular oxygen distribution in awake hamster window chamber model during hyperoxia. *Am J Physiol Heart Circ Physiol* 2003; 285:H1537-H1545.
52. Assaly R A, Azizi M, Kennedy D, et al.: Plasma expansion by polyethylene-glycol-modified-albumin. *Clin Sci* 2004; 107:263-272.
53. Cronnenwett J L and Lindenauer S M: Direct measurement of arteriovenous anastomotic blood flow in the septic canine hindlimb. *Surgery* 1979; 85:275-282.
54. Bateman R M, Jagger J E, Sharpe M D, et al.: Erythrocyte deformability is a nitric oxide-mediated factor in decreased capillary density during sepsis. *Am J Physiol Heart Circ Physiol* 2001; 280:H2848-56.
55. Colasanti M and Suzuki H: The dual personality of NO. *Trends Pharmacol* 2000; 21:249-252.
56. Feihl F, Waeber B and Liaudet L: Is nitric oxide overproduction the target of choice for the management of septic shock? *Pharmacol Ther* 2001; 91:179-213.
57. Minamiyama Y, Takemura S and Inoue M: Albumin is an important vascular tonus regulator as a reservoir of nitric oxide. *Biochem Biophys Res Comm* 1996; 225:112-115.

Example II

Hemorrhagic Shock Resuscitation Using PEG-Albumin

I. Introduction

The present study was carried out using the cell-impermeant form of the H+-sensitive fluorochrome 2',7'-bis-(2-carboxyethyl)-5,6-carboxyfluorescein (BCECF, Molecular Probes, Eugene, Oreg.) injected intravenously to assess tissue pH in the microcirculation of the hamster window chamber model subjected to a conventional hemorrhagic shock and resuscitation procedure. Resuscitation was performed using a volume infusion of 10% hydroyethylstarch (HES) 200 or 2.5% polyethylene glycol conjugated bovine albumin (PEG-Alb), materials with similar molecular weight but different colloidal osmotic pressure (COP).

II. Materials and Methods

Animal preparation. Investigations were performed in male Golden Syrian Hamsters fitted with a dorsal chamber window (20, 21). This model has been extensively used for investigations of the intact microvasculature of adipose and subcutaneous tissue and skeletal muscle in conscious animals for extended periods (9-11). Pentobarbital sodium (50 mg/kg, i.p.) is used for window implantation and for carotid artery and jugular vein catheterization. Four to five days after the initial surgery the microvasculature is examined and only animals passing an established systemic and microcirculatory inclusion criteria, which includes having tissue void of low perfusion, inflammation, edema were entered into the study (22). Animal handling and care followed the "NIH Guide for the Care and Use of Laboratory Animals". Experimental protocol was approved by the local animal care committee.

Blood chemistry and biophysical properties. Arterial blood was collected in heparinized glass capillaries (0.05 ml) and immediately analyzed for $paO_2$, $paCO_2$, base excess (BE) and pH (Blood Chemistry Analyzer 248, Bayer, Norwood, Mass.). The comparatively low $paO_2$ and high $paCO_2$ of these animals is a consequence of their adaptation to a fossorial environment. Blood samples for viscosity and colloid osmotic pressure measurements were quickly withdrawn from the animal with a heparinized 5 ml syringe at the end of the experiment for immediate analysis. Viscosity was measured in a DV-II pluss (Brookfield Engineering Laboratories, Middleboro, Mass.). Colloid osmotic pressure was measured using a 4420 Colloid Osmometer (Wescor, Logan, Utah).

Hemoglobin oxygen saturation. The oxygen equilibrium curve (OEC) for hamster red blood cells (RBCs) was investigated by deoxygenation of oxygen-equilibrated oxy-Hb in the Hemox buffer (pH 7.4) at 37.6° C., using a Hemox Analyzer (TCS Scientific Corporation, New Hope, Pa.). The analyzer measures the $O_2$ pressure with a Clark-type $O_2$ electrode (Yellow Springs Instrument, OH) and simultaneously calculates the Hb saturation via a dual-wavelength spectrophotometer. Changes in pH were set adding Tris and BisTris buffers to the Hemox buffer (6.90, 7.25, 7.40). Tris and BisTris buffers were prepared by fully titrating the reagents with HCl before adjusting the pH of the solutions. In this way, the concentration of $Cl^-$ ions was equal to the buffer at all pH values.

pH measurements. The cell-impermeant BCECF was injected into the jugular catheter (0.7 mg/kg). After 15 min, fluorescence emission signals (535-nm filter; Thorslabs Inc., Newton, N.J.) were recorded using a photomultiplier (Hamamatsu R928) following 495-nm (pH sensitive) and 440-nm (concentration sensitive) excitation (Thorslabs). The fluorescence ratio gives concentration-independent, pH-sensitive fluorescence measurements (23, 24). The fluorescent ratio was formed as follows: $R535=(I_{495}-I_{back495})/(I_{440}-I_{back440})$. Background fluorescent intensities for each wavelength ($I_{back495}, I_{back495}$) were recorded before dye injection and subtracted from the corresponding fluorescence intensities. Probe fluorescence at 440 and 495-nm was typically 4 to 8 times higher than the corresponding background-fluorescence.

Fluorescence excitation. The areas of interest were located with the microscope, and the edge of the vessels were used to focus the image with both bright field trans-illumination and fluorescence epi-illumination. Average fluorescence intensities were recorded before and after the tissue was excited with 495-nm for 5 seconds. The filter wheel was rotated in order to pass 440-nm and the average fluorescence intensities were again recorded. To circumvent optical problems associated with quantitative microscopy of thick tissues, a partial confocal effect was used by placing a 150 μm pin-hole in the excitation light path (24).

Fluorescence emission measurements. The fluorescence level of BCECF at 535-nm was evaluated by using a photomultiplier (Hamamatsu R928). The photomultiplier was powered with a socket assembly (Hamamatsu C6270) and enclosed in a Faraday cage configuration, minimizing noise. The only connections to the unit were a 15V DC supply and the signal output via a coaxial shielded cable. A single voltage divider potentiometer was used to regulate the photomultiplier voltage divider high voltage supply (0-1000 V). The photometric head was mounted on the camera port of the trinocular head of the microscope.

The optics of the photometric assembly and the Olympus BX51WI were combined in such a fashion that an adjustable rectangular diaphragm, which is mounted in the photometric unit, is back illuminated and visualized through a binocular observation port with exact size and configuration and superimposed on the field of view. This design allows us to know the precise location of the photometric window relative to the anatomical details of the tissue under study. The plane of optical sectioning was fixed for all the blood vessels in the same location of the vessel wall of each microvessel and was visualized in sharp focus by fluorescence microscopy. The signal output from the photomultiplier can be calibrated in terms of the number of detected photons per unit area of emission. The photomultiplier current output is measured as a voltage across a 10 kΩ resistor, and its gain is $10^7$ at the design voltage of 1000 V, thus a 1V signal corresponds to $10^{-11}$ A of anode current. In the present configuration signal-to-noise is estimated to be on the order of 100:1, and noise-free signals are detected with the oscilloscope amplifier at a gain of 10. Phosphorescence in the experiments was detected in the range of 0.5-1.0 V with a window size of 15×15 μm referred to the anatomy under study. Quantum efficiency of the system in the 450 to 550-nm band is 70%, therefore the minimal signal (0.8 V) corresponds to a photon flux of about $9.6×10^6$ photons/sec m$^2$.

Calibration. In vitro calibration. BCECF solutions (0.02 mg/ml) at various pH were prepared using a sodium phosphate monobasic/dibasic buffer system at 300 mOsm, near physiologic osmolarity. The buffer system provided a pH range from 4 to 10. Glass microcapillaries 40 μm internal diameter (Dynamics, Inc., Rockaway, N.J.) were soaked in doubly distilled and deionized water for 5 min, dried at room temperature for approximately 10 min, and then filled in the respective pH solutions. Fluorescence intensities were measured at different locations as described above. The same procedure was performed on two extra sets of buffers to yield a total of three measurements at a given buffer pH.

Tissue pH calibration. The cover glass of the window chamber tissue from sacrificed animals was removed and the tissue was suffused. The tissue serosal surface was covered with a buffer containing 110 mM KCl, 10 mM HEPES tris (hydroxymethyl)aminomethane (Tris), and adding HCl/NaOH to obtain different pH values between 6.0 and 8.0 (25).

Experiments with capillary tubes in vitro as well as excised tissues (normal skin) showed that ratios of fluorescence intensity were linearly proportional ($r^2 > 0.96$) to pH in the physiological range of 6.0-8.0 (26). This fluorescent ratio technique was applicable only for interstitial pH measurements. It did not apply to vascular locations, as light absorption by blood hemoglobin differed for the two excitation wavelengths used (26). Interstitial pH values were measured at a distance $>10$ μm from the nearest vessel wall, when the portion of the tissue illuminated did not overlap with microvessels.

In vivo protocol. The unanesthetized hamster, supported in a custom-made cradle, was placed on the microscope (BX51WI, Olympus, New Hyde Park, N.Y.) and the window chamber was secured on the stage. The tissue image was projected onto a charge-coupled device camera (COHU 4815) connected to a videocassette recorder (AG-7355; NC) and viewed on a monitor. Measurements were carried out using a 40× (LUMPFL-WIR, numerical aperture 0.8, Olympus) water immersion objective. For easier detection of RBC passage, the contrast between RBCs and tissue was enhanced with a BG12 (420 nm) bandpass filter. The chamber vascular architecture was recorded by scanning the entire chamber area using trans-illumination. Approximately 10-20 sites were selected and background images (no fluorochrome in tissue) at both wavelengths were acquired.

Functional capillary density (FCD). FCD is defined as the number of capillary segments with transit of at least a single RBC in a 30 s period per microscopic observation field. This parameter is evaluated in 12 successive microscopic fields (totaling a region of ~1.6 mm$^2$, 420×320 μm each) by systematically displacing the microscopic field of view by a field width in successive steps in the lateral direction. The first field is chosen by a distinctive anatomic landmark (i.e., large microvascular bifurcation) to easily and quickly reestablish the same observation fields at each observation time point. Each field has between 5 and 12 capillary segments with RBC flow. FCD (cm$^{-1}$), i.e., total length of RBC perfused capillaries divided by the area of the microscopic field of view, is evaluated by measuring and adding the length of capillaries with RBC transit in the field of view.

Microhemodynamic parameters. Arteriolar and venular blood flow velocity were measured on-line using the photodiode cross-correlation technique (27) (Fiber Optic Photo Diode and Velocity Tracker Model 102B; Vista Electronics, San Diego). The centerline velocity (V) was corrected according to vessel size to obtain the mean RBC velocity (28). The video image shearing technique was used to measure vessel diameter (D) on-line (29). Blood flow was calculated from the measured parameters as $Q=\pi V \times (D/2)^2$.

Microvascular pO$_2$ distribution. High resolution non-invasive microvascular pO$_2$ measurements were made using phosphorescence quenching microscopy (PQM) (22, 30). PQM is based on the oxygen-dependent quenching of phosphorescence emitted by albumin-bound metalloporphyrin complex after pulsed light excitation. PQM is independent of the dye concentration within the tissue and is well suited for detecting hypoxia because its decay time is inversely proportional to the pO$_2$ level, causing the method to be more precise at low pO$_2$s. This technique is used to measure both intravascular and extravascular pO$_2$ since the albumin-dye complex continuously extravasates the circulation into the interstitial tissue (22, 30). Tissue pO$_2$ was measured in tissue regions in between functional capillaries. PQM allows for precise localization of the pO$_2$ measurements without subjecting the tissue to injury. These measurements provide a detailed understanding of microvascular oxygen distribution and indicate whether oxygen is delivered to the interstitial areas.

The system setup has been described in previous references (30). Animals received a slow intravenous injection of 15 mg/kg bw at a concentration of 10.1 mg/ml of a palladium-meso-tetra(4-carboxyphenyl) porphyrin (Pd-TCPP; Porphyrin Products, Inc., Logan, Utah) which was allowed to circulate for 20 minutes prior to pO$_2$ measurements. The phosphorescence was excited by pulsed light (30 Hz, 4 μsec duration) for a period of <5 sec, the measurement site was microscopically vignetted by an adjustable slit. For intravascular measurements, an optical rectangular slit approximately 5 by 35 μm was positioned longitudinally within the vessel of interest. For interstitial tissue measurements, a 15 by 10 μm slit was placed in intercapillary spaces in regions void of large vessels. The phosphorescence decay curves were analyzed off-line, using a standard single exponential least squares numerical fitting technique and the resultant time constant was applied to the Stern-Volmer equation to calculate pO$_2$, using predetermined parameters of $\tau_o$ and $k_q$ corrected for this animal model (30).

Pd-TCPP emission is temperature and pH dependent (31). Previous work established the correction factor for pH dependency of $k_q$ (32). The pH dependency of $\tau_o$ was much less than $k_q$, and did not require correction (32).

Oxygen delivery and extraction. The microvascular methodology used in the present studies allows a detailed analysis of oxygen supply in the tissue. Calculations of oxygen delivery, O$_2$ $_{delivery}$ defined as amount of oxygen per unit time delivered by the arterioles to the microcirculation normalized relative to control, and extraction, O$_2$ $_{extraction}$ defined as the amount of oxygen released by blood in the microcirculation per unit time normalized relative to control, are made using equation 1 and 2 (33):

$$O_{2\ delivery} = [(RBC_{Hb} \times \gamma \times S_A\%) + (1-Hct) \times \alpha \times pO_{2\ A}] \times Q \qquad (1)$$

$$O_{2\ extraction} = [(RBC_{Hb} \times \gamma \times S_{A-V}\%) + (1-Hct) \times \alpha \times pO_{2\ A-V}] \times Q \qquad (2)$$

where RBC$_{Hb}$ is the hemoglobin in RBCs expressed in grams per dl of blood, Plasma$_{Hb}$ is the cell free hemoglobin in grams per dl of blood, γ is the oxygen carrying capacity of hemoglobin at 100% saturation or 1.34 ml O$_2$/g Hb, S$_A$% is the arteriolar oxygen saturation of RBCs, (1−Hct) is the fractional plasma volume and converts the equation from per dl of plasma to per dl of blood, α is the solubility of oxygen in plasma equal to 3.14×10$^{-3}$ ml O$_2$/dl plasma mmHg, pO$_{2\ A}$ is the arteriolar partial pressure of oxygen, pO$_{2\ A-V}$ is the arteriolar/venular difference in pO$_2$), and Q is the microvascular flow for each microvessel as percent of baseline. The OECs were determined as previously described. In this analysis microvascular hematocrit was corrected according to the findings of Lipowsky and Firrell (34).

Acute hemorrhage and volume replacement protocol. Acute hemorrhage was induced by withdrawal of 50% of estimated total blood volume via the carotid artery catheter within 5 min. Total blood volume was estimated as 7% of body weight. One hour after hemorrhage induction, animals received a single volume infusion of 50% of BV of 10% HES 200 or 2.5% PEG-Alb within 10 min via the jugular vein catheter. Animals did not receive any additional fluid during the experiment. Fifty percent of shed blood volume was used because autotransfusion restores about half of the shed volume during shock; therefore, restoration of 100% of the blood volume withdrawn causes hypervolemia. Parameters were analyzed before hemorrhage (baseline), after hemorrhage (shock), and up to 90 min after volume replacement (resuscitation). Tissue pH was measured continuously at baseline, shock and resuscitation. Partial oxygen tension values were determined only once at the end of the experiment to avoid micro-hemodynamic side effects from excessive light exposure and porphyrin excitation.

Test materials. PEG-Alb. Albumin (bovine serum albumin; Sigma-Aldrich, St. Louis, Mo.) was PEG conjugated using single step version of the thiolation mediated, maleimide chemistry based conservation PEGylation described by Acharya et al. (35). Albumin (0.25 mM) was incubated overnight with 5 mM 2-iminothiolane (BioAffinity Systems, Rockford, Ill.) and 7.5 mM maleimide phenyl PEG-5000 in phosphate buffer saline (PBS). The surface amino groups are thiolated and thiol groups generated on the protein in situ are derivatized by the maleimide PEG in the reaction mixture. The single step reaction limits the oxidation of the thiols of the thiolated protein to generate dimers and polymers of BSA, and is the preferred approach to generate PEGylated proteins. Excess reagents were removed by tangential flow filtration using the Minim System (Pall Life Sciences, Ann Arbor, Mich.) after overnight incubation. A 70 kDa membrane was used for diafiltartion for removal of unreacted PEG and excess immunothiolane. After diafiltration PEG-Alb was concentrated to 2.5 g/dL (protein based). The extent of PEGylation in this sample was measured by nuclear magnetic resonance, and showed an average of nearly 12 copies of PEG 5K chains conjugated to an albumin molecule, yielding to 130 kDa of calculated molecular weight, and a molecular radius of 8 to 9 nm. At the concentration of a 2.5 g/dl PEG-Alb (protein mass based) solution has COP of 37.6 mmHg, and viscosity is 2.0 cp.

Hydroxyethyl starch (HES). This material (Pentaspan, B. Braun Medical, Irvine, Calif.) was formulated at 10% w/vol in 0.9% saline and was used as a colloid control solution whose principal properties are: COP of 85 mmHg and a viscosity of 3.4 cp.

Experimental groups. Before the experiment, animals were randomly divided into the following experimental groups: 1) resuscitation with 10% HES 200 (group labeled HES); 2) resuscitation with 5% MALPEG-Alb (group labeled PEG-Alb); and 3) an additional group of animals were not resuscitated (group labeled SHAM).

Data analysis. Results are presented as mean±standard deviation unless otherwise denoted. Data within each group were analyzed using one way analysis of variance ANOVA and when appropriate post hoc analyses performed with the Bonferroni's multiple comparison test. All data are presented as absolute values and ratios relative to baseline values. A ratio of 1.0 signifies no change from baseline while lower and higher ratios are indicative of changes proportionally higher and lower than baseline. The same vessels and functional capillary fields were followed, allowing direct comparisons (repeated measurements) to their baseline levels producing a more robust statistics for small sample populations. All statistics were calculated using GraphPad Prism 4.01 (GraphPad Software, Inc., San Diego, Calif.). Changes were considered statistically significant if P<0.05.

III. Results

A total of 18 animals (62.4±4.7 g) were studied. Animals were assigned randomly to the experimental groups: HES (n=6; 63.1±6.1 g); PEG-Alb (n=6; 62.4±4.7 g) and SHAM (n=6; 62.9±5.2 g).

Systemic parameters. All groups showed a significant reduction of Hct after hemorrhagic shock (49±1% for baseline, 31±1% after shock). Resuscitation decreased Hct further to 23±1% and 22±1% with HES and PEG-Alb (P<0.001 for both groups compared to baseline). Hemoglobin showed the same trend (14.8±0.7 $g_{Hb}$/dl for baseline, 10.3±0.6 $g_{Hb}$/dl 50 min after shock, 7.5±0.4 and 7.1±0.4 $g_{Hb}$/dl 60 min after resuscitation with HES and PEG-Alb (P<0.001 compared to baseline). At 90 min after resuscitation Hct was: HES, 22±1%; PEG-Alb, 22±1%; and, SHAM, 28±2%.

Figure 10:
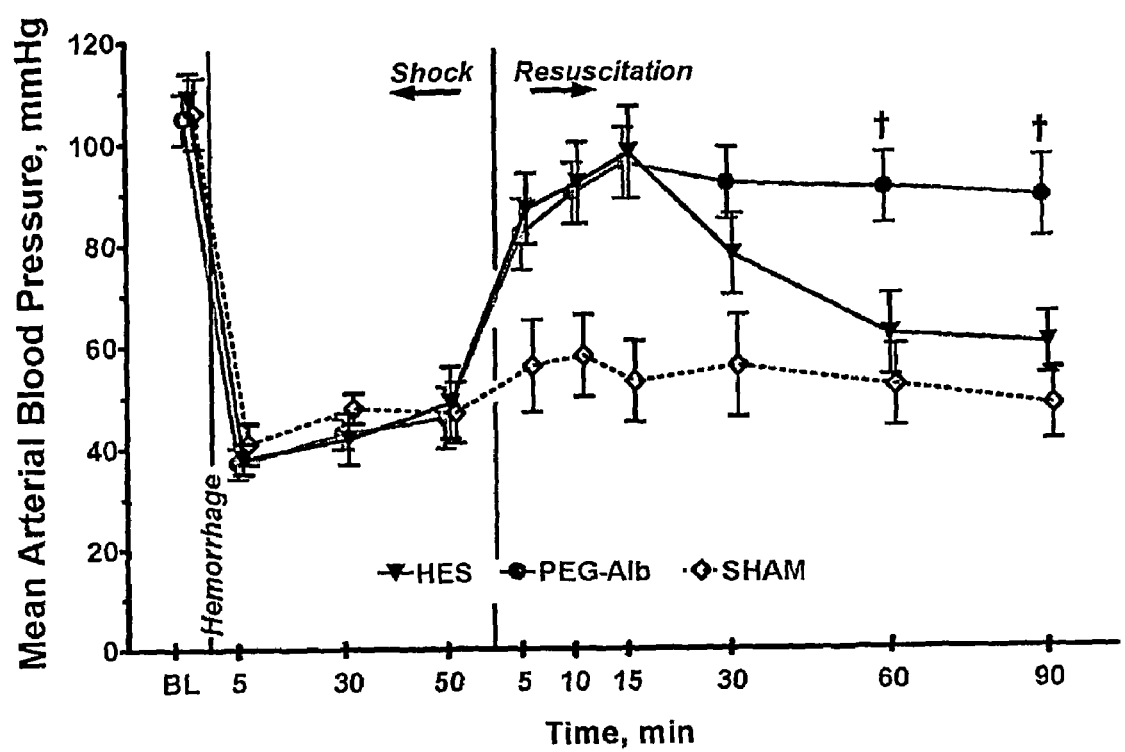
FIG. 10. Mean arterial blood pressure. Broken line represents baseline level. †: significantly different between HES and PEG-Alb (P<0.05).

MAP before hemorrhage was 107±6 mmHg, which decreased to 39±5 mmHg 5 min after shock and recovered to 48±6 mmHg before resuscitation. Changes over time for MAP in all the groups are presented in FIG. 10. Ninety minutes after resuscitation with HES and PEG-Alb, MAP recovered to 60±6 and 89±8, respectively. HES and PEG-Alb groups reached the highest pressure after 15 min. Blood pressure in the PEG-Alb group was gradually increased and was sustained, opposite to the HES group which began to decrease 15 min after resuscitation. HR was not affected significantly during hemorrhagic shock and resuscitation.

Laboratory parameters. Changes in systemic and blood gas parameters prior to hemorrhagic shock are presented in Table 5. Systemic arterial blood gas analysis showed a statistically significant rise in arterial $pO_2$ from baseline after shock and resuscitation for all solutions. Arterial $pCO_2$ was statistically changed from baseline in all the experimental groups after shock and after resuscitation with HES (P<0.05 compared to baseline). Arterial blood pH was statistically changed from baseline in all the experimental groups by hemorrhagic shock and recovered after resuscitation. Blood base excess (BE) was statistically significantly decreased after shock and remained decreased post resuscitation with HES (P<0.05). Resuscitation with PEG-Alb recovered blood BE 60 min after resuscitation.

Total blood lactate showed a statistical significant increase after shock and remained increased; post resuscitation in the HES group compared to baseline (P<0.05). Lactate baseline level for the PEG-Alb group was recovered 60 min after resuscitation (P<0.05).

Figure 11:
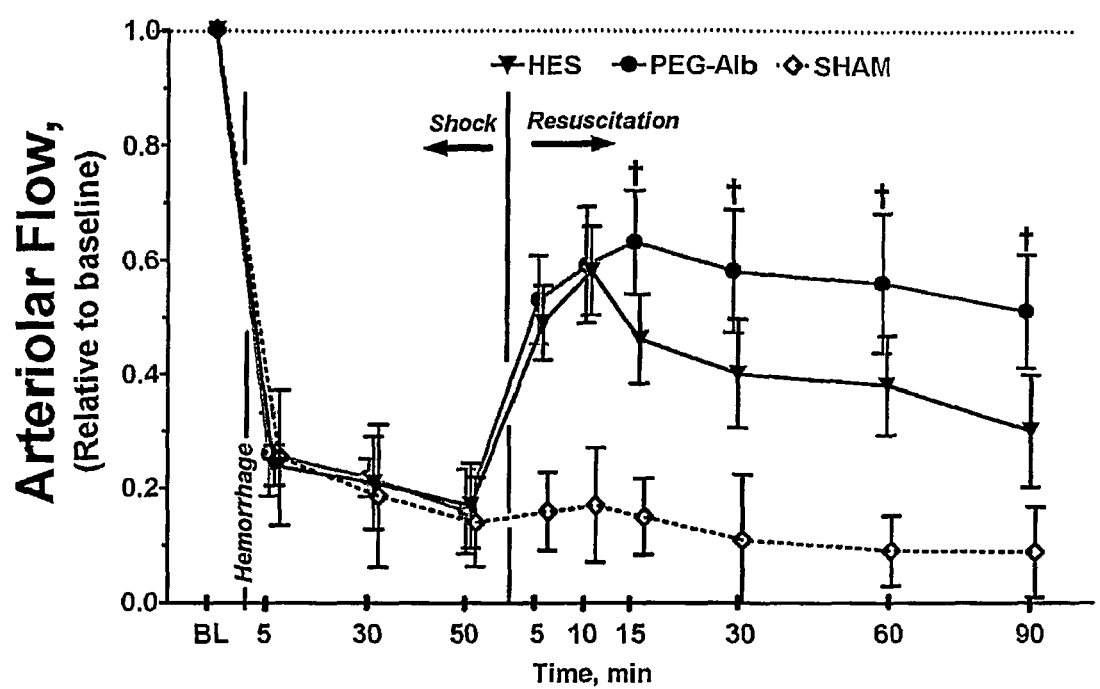
FIG. 11. Computed arteriolar blood flow. Table 6 in Example II presents detailed microvascular information. Broken line represents baseline level. †: significantly different between HES and PEG-Alb (P<0.05).

Microhemodynamics. Changes in diameter, RBC velocity and blood flow were measured 10 min after hemorrhagic shock and 60 min after resuscitation. Large feeding and small arcading arterioles (range 45-70 μm) and small collecting and large venular vessels (range 45-75 μm) were included in the study. Table 6 presents arteriolar and venular hemodynamics. FIG. 11 presents arteriolar blood flow, during shock and after resuscitation for each experimental group.

There were no statistically significant differences among the three groups in microvascular diameter, RBC velocity and blood flow at baseline and during the shock period up to the time of resuscitation. Hemorrhage resulted in arteriolar vasoconstriction in the range of 0.80 to 0.95 of baseline. Venular diameters decreased to values in the range of 0.85 to 0.95 of baseline. Change was statistically significant according to the repeated measures ANOVA test (Bonferroni's multiple comparison, P=0.048). The reduction in RBC velocity and the computed blood flow were more pronounced 50 min after the hemorrhagic shock. RBC velocity decreased during shock to 0.15 to 0.25 of baseline in arterioles and to values in the range of 0.18 to 0.24 of baseline in venules. PEG-Alb resuscitation increased RBC velocity significantly compared to the HES group to about 70% in arterioles and 80% in venules.

Figure 12:
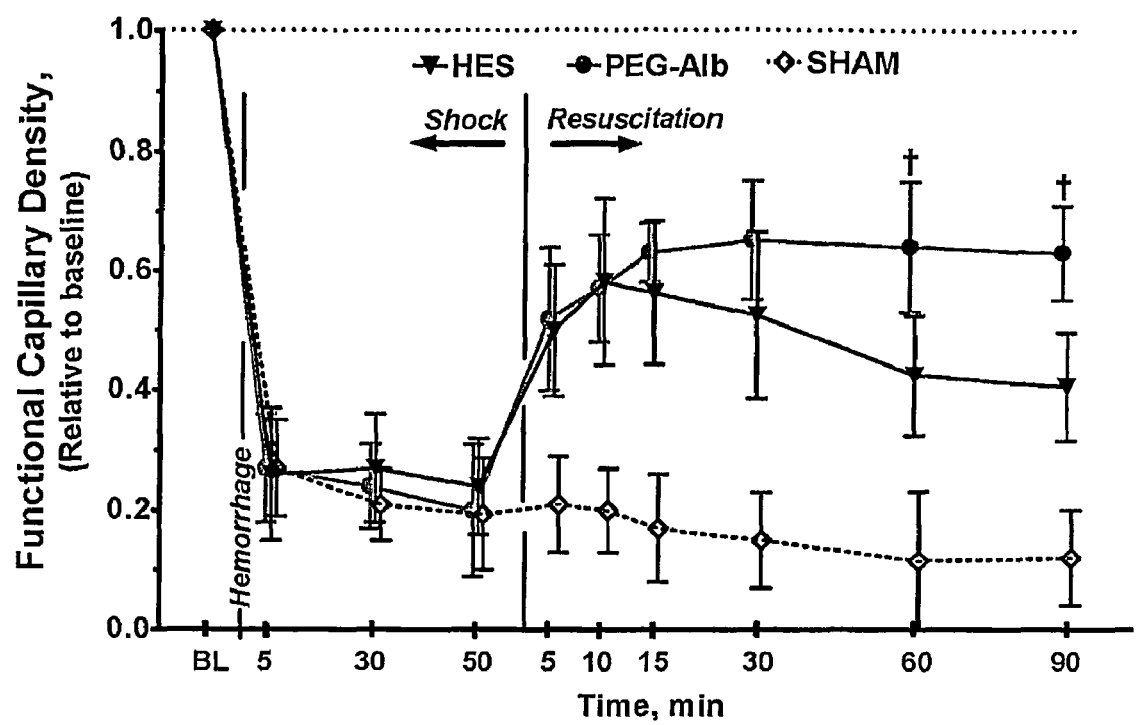
FIG. 12. Functional capillary density (FCD). †: significantly different between HES and PEG-Alb (P<0.05).

Functional capillary density. FIG. 12 presents the changes over time for FCD in all the groups. Withdrawal of 50% of the BV consistently lowered FCD to values in the range of 20% to 30% of baseline. Resuscitation with HES resulted in a maximal increase of FCD 10 min after resuscitation, while PEG-Alb showed a gradual recovery in FCD which was sustained over 90 minutes. All values were significantly lower than baseline.

Physical properties of blood. Table 7 compares blood rheological properties and COP 90 min after resuscitation. Blood and plasma viscosities were significantly different from baseline. Blood viscosity was reduced 50% after resuscitation, and plasma viscosity was preserved. Colloid osmotic pressure was statistically reduced in the group without resuscitation. Nondiluted blood values for rheological properties and colloid osmotic pressures were also obtained from hamsters that did not undergo the shock protocol.

Figure 13:
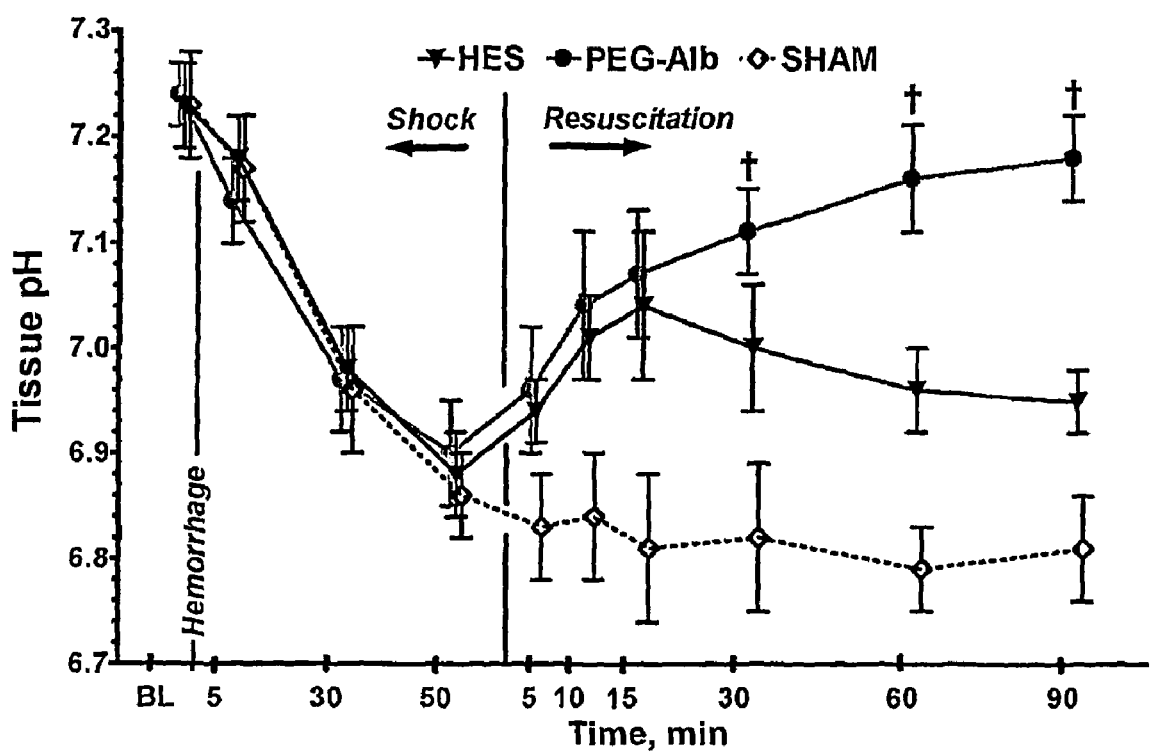
FIG. 13. Tissue pH. †: significantly different between HES and PEG-Alb (P<0.05).

Interstitial pH. FIG. 13 presents the changes over time for pH in all groups. Hemorrhage consistently lowered pH during shock period. Resuscitation with PEG-Alb recovered pH to baseline levels, while HES recuperated pH for a brief period without sustaining recovery over time.

Figure 14:
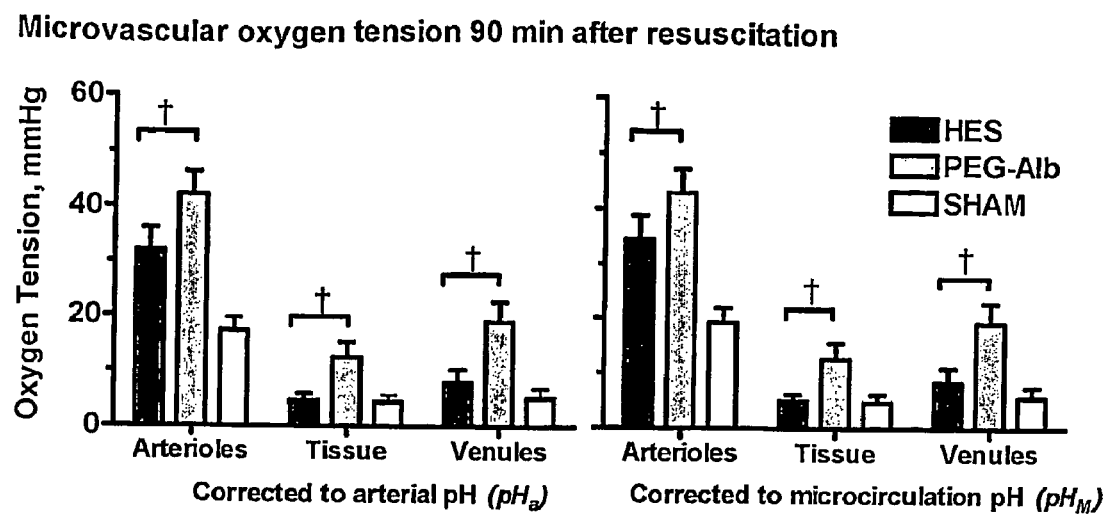
FIG. 14. Intravascular and tissue oxygen partial pressure measured with phosphorescence quenching microscopy (PQM). Tissue pH was evaluated in small areas next to the vessels. PEG-Alb showed higher oxygen on intravascular and tissue than the HES resuscitation group. The use of the microcirculation or arterial pH to convert the phosphorescent lifetimes to oxygen pressure did not change the results from these measurements, since the maximum change in oxygen levels due to the pH correction was less than 10%. †: significantly different between HES and PEG-Alb (P<0.05).

Intravascular partial pressure of oxygen. FIG. 14 presents intravascular and tissue $pO_2$ 90 min after resuscitation. Resuscitation with PEG-Alb led to a tissue oxygen tension of 12±3 mmHg (13±3 mmHg after correction for microcirculation pH). This was significantly higher than the values obtained after resuscitation with RES ($P<0.05$), which were 5±1 mmHg (5±1 mmHg after correction for microcirculation pH). Oxygen tension in arterioles was 42±4 mmHg after resuscitation with PEG-Alb (43±4 mmHg after correction for microcirculation pH) compared to 32±4 mmHg with HES (34±4 mmHg after correction for microcirculation pH) ($P<0.05$). Venular $pO_2$ was 8±2 mmHg after resuscitation with HES (8±3 mmHg after correction for microcirculation pH) compared with 19±3 for resuscitation with PEG-Alb (19±4 mmHg after correction for microcirculation pH) ($P<0.05$). Control data for microvascular $pO_2$ was obtained from a database, which includes many independent experiments carried out using the same animal model. Calculations of oxygen delivery and extraction showed significantly higher values after volume restitution with PEG-Alb than when HES was used ($P<0.05$).

Figure 15:
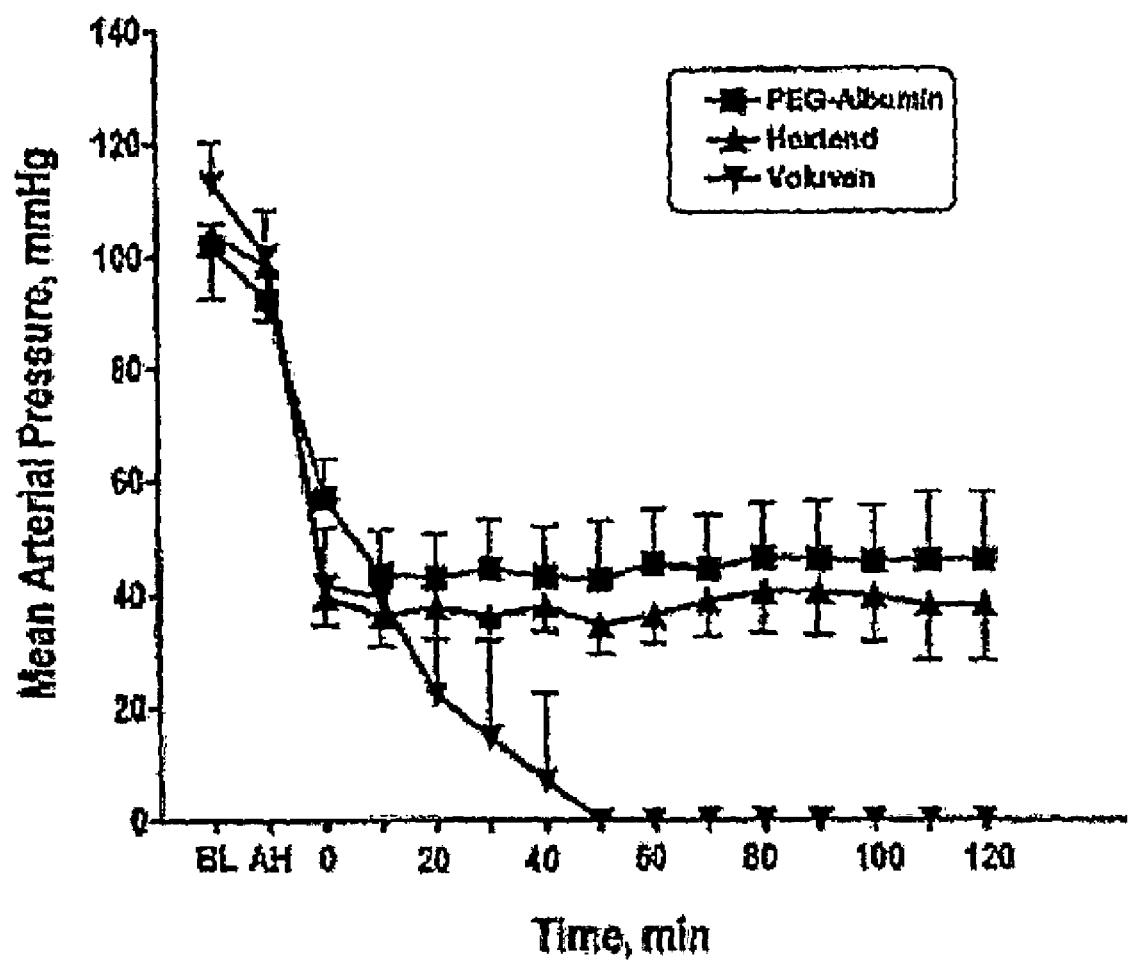
FIG. 15. Hemodilution/Exponential Bleed. Time course of the mean arterial pressure changes with Peg-Albumin, Hextend and Voluven. BL, baseline; AH, acute hemodilution. The exponential bleed of 60% of the animal's blood volume is during the 1st hr after AH. At 60 min, the exponential bleed is stopped and the animals are monitored. The large deviations in the Voluven group are due to the drop out of animals over time due to death.
Figure 16:
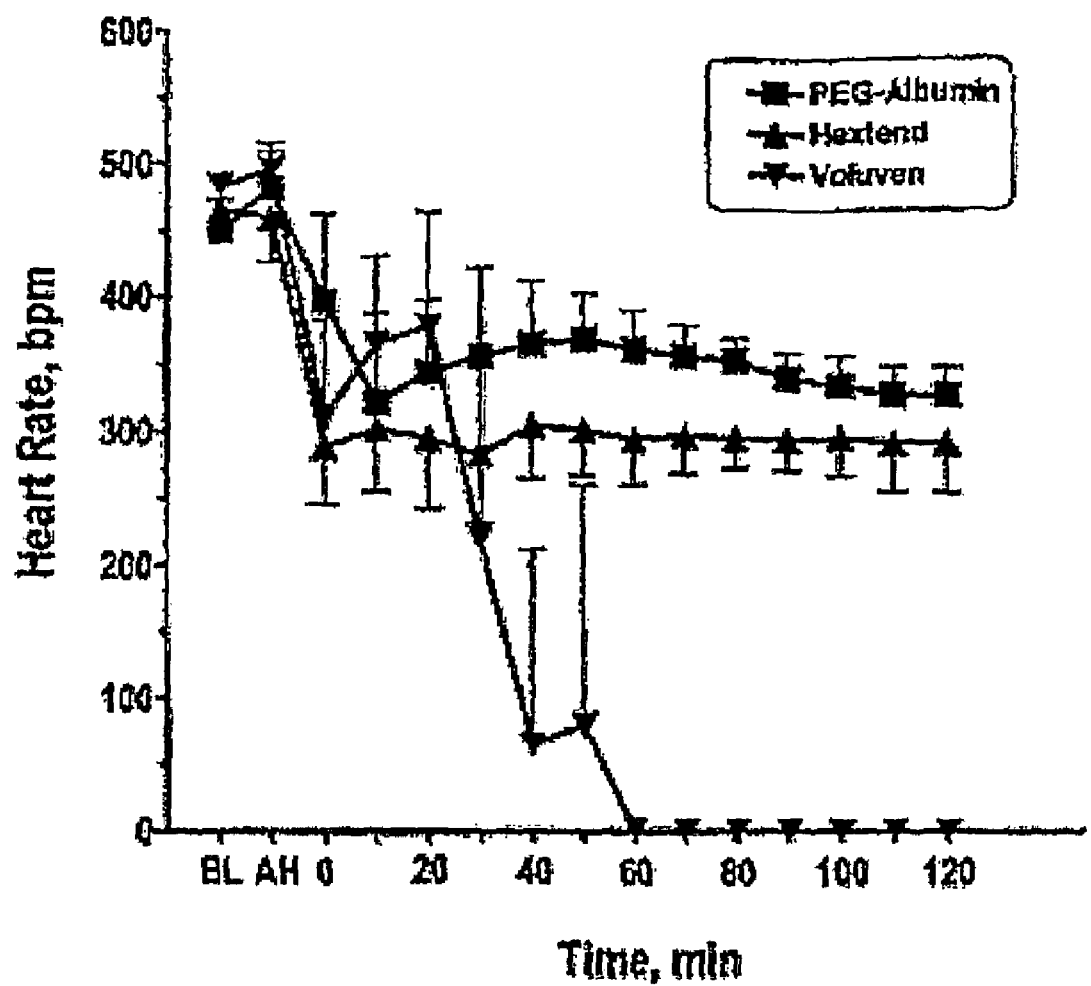
FIG. 16. Hemodilution/Exponential Blood. Time course of the heart rate changes with Peg-Albumin, Hextend and Voluven. BL, baseline; AH, acute hemodilution. The exponential bleed of 60% of the animal's blood volume is during the 1st hr after AH. At 60 min, the exponential bleed is stopped and the animals are monitored. The large deviations in the Voluven group are due to the drop out of animals over time due to death.
Figure 17:
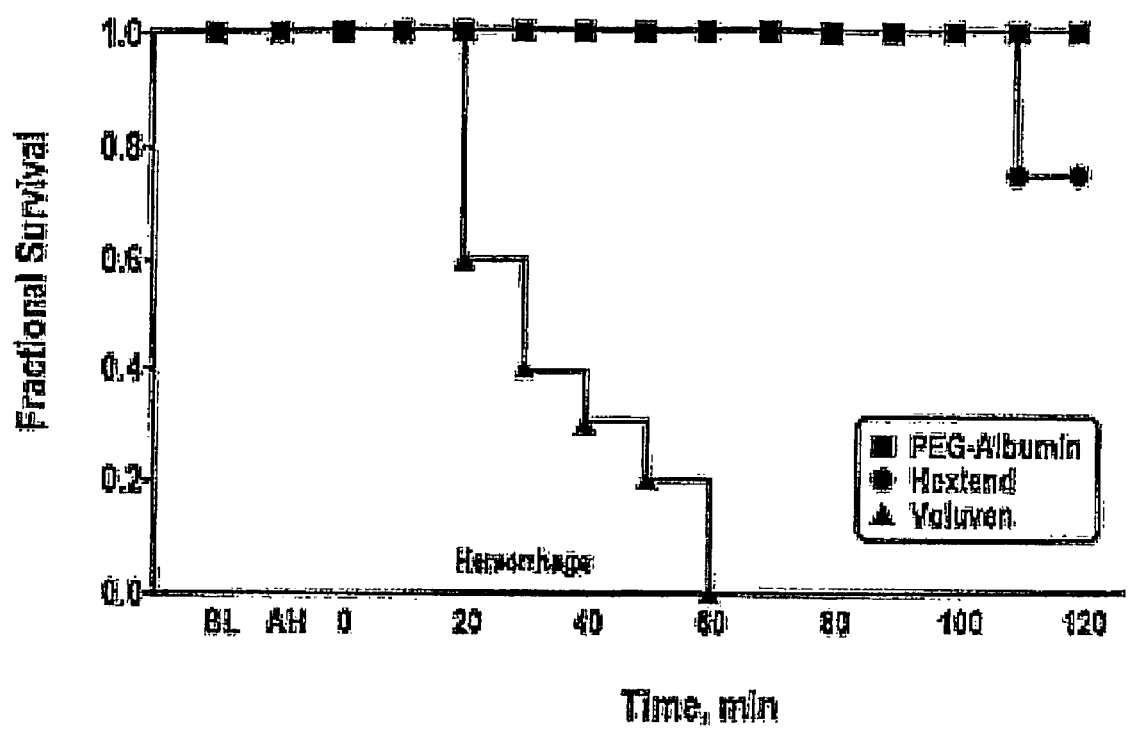
FIG. 17. Hemodilution/Exponential Blood. Comparison of the survival for the three treatment groups: Peg-Albumin, Hextend and Voluven. Death is considered when MAP is less than 30 mmHg for more than 10 minutes.

Acute hemodilution and exponential bleed model. Experiments were performed in the hamster window chamber to determine the effectiveness of the PEG-albumin solution in a protocol designed to simulate a clinical scenario where the patient is given fluid during surgery, becomes hemodiluted, and then has a severe uncontrolled hemorrhage (exponential bleed) which comes under surgical control after an hour. The solutions studied were 4% PEG-HSA, Hextend (Biotime Inc, hydroxyethyl starch solution, 500 MW) and Voluven (hydroxyethyl starch solution, 130 MW). The animals were first subjected to an exchange transfusion with a plasma expander. The volume of exchange was 50% of the blood volume (estimated as 7% of the animal's body weight). Following this the animals were subjected to an exponential hemorrhage over the next hour where 60% of their blood volume was withdrawn. FIGS. 15 and 16 show the changes in mean arterial pressure (MAP) and heart rate (HR) for the animals in each group (n=5). Both PEG-HSA and Hextend recovered blood pressure to higher and sustained levels as compared to the Voluven treated group. The change in the heart rate followed a similar pattern with the PEG-HSA appearing to maintain a higher FIR initially during the hemorrhage period. The survival plot (FIG. 17) shows that all PEG-HSA animals were able to survive the period of observation, 1 hr after the end of the exponential bleed as compared to the other two treatment groups. Death is considered when MAP is less than 30 mmHg for more than 10 minutes.

Laboratory Parameters During Shock Resuscitation.

TABLE 1

| | Hct % | Hb g/dl | BP mmHg | HR bpm | pH | $pO_2$ mmHg | $pCO_2$ mmHg | BE mmoL/L | Lact mmol/l |
|---|---|---|---|---|---|---|---|---|---|
| Baseline | | | | | | | | | |
| HES | 49 ± 1 | 14.8 ± 0.6 | 109 ± 6 | 427 ± 29 | 7.36 ± 0.02 | 60 ± 5 | 56 ± 6 | 5.3 ± 2.4 | 1.3 ± 0.4 |
| PEG-Alb | 50 ± 2 | 14.9 ± 0.7 | 105 ± 5 | 434 ± 26 | 7.35 ± 0.02 | 62 ± 6 | 57 ± 7 | 4.3 ± 2.7 | 1.2 ± 0.5 |
| SHAM | 49 ± 1 | 14.7 ± 0.5 | 108 ± 7 | 430 ± 30 | 7.36 ± 0.02 | 59 ± 7 | 59 ± 7 | 3.7 ± 2.8 | 1.4 ± 0.5 |
| Shock (50 min) | | | | | | | | | |
| HES | 30 ± 2§ | 10.1 ± 0.7§ | 46 ± 6§ | 466 ± 28 | 7.28 ± 0.05§ | 101 ± 12§ | 40 ± 6§ | −5.4 ± 3.2§ | 5.4 ± 0.8§ |
| PEG-Alb | 31 ± 1§ | 10.6 ± 0.4§ | 49 ± 7§ | 475 ± 29 | 7.27 ± 0.06§ | 99 ± 14§ | 41 ± 7§ | −5.7 ± 3.5§ | 5.9 ± 1.1§ |
| SHAM | 31 ± 1§ | 10.3 ± 0.6§ | 47 ± 6§ | 469 ± 27 | 7.29 ± 0.05§ | 103 ± 12§ | 38 ± 7§ | −5.3 ± 3.1§ | 4.8 ± 1.0§ |
| Resuscitation (60 min) | | | | | | | | | |
| HES | 23 ± 1§† | 7.5 ± 0.4§† | 62 ± 8§† | 440 ± 32 | 7.31 ± 0.04† | 96 ± 12§ | 43 ± 6§ | −1.4 ± 3.4§ | 2.9 ± 0.8§† |
| PEG-Alb | 22 ± 1§† | 7.1 ± 0.5§† | 91 ± 7§† | 418 ± 28 | 7.37 ± 0.05† | 90 ± 11§ | 54 ± 7† | 1.5 ± 2.7† | 1.8 ± 0.5† |
| SHAM | 29 ± 1§† | 9.1 ± 0.6§† | 52 ± 8§ | 382 ± 36 | 7.27 ± 0.06§ | 122 ± 14§ | 34 ± 9§ | −6.8 ± 3.8§ | 6.5 ± 1.6§ |

Values are means ± SD.

Hct, systemic hematocrit;

[Hb], hemoglobin content of blood;

[MAP], mean arterial pressure;

[HR], heart rate;

[BE], base excess;

[Lact], lactate.

§significant different as compared to baseline:

†compared to shock ($P < 0.05$).

Microhemodynamic Parameters During Shock Resuscitation.

TABLE 2

| | Arteriolar | | | Venular | | |
|---|---|---|---|---|---|---|
| | Diameter μm | RBC Velocity mm/s | Flow nl/s | Diameter μm | RBC Velocity mm/s | Flow nl/s |
| | Baseline | | | | | |
| HES | 59 ± 9 | 4.5 ± 1.2 | 11 ± 7 | 63 ± 11 | 1.7 ± 0.9 | 5 ± 4 |
| PEG-Alb | 58 ± 8 | 4.3 ± 1.1 | 10 ± 6 | 62 ± 10 | 2.0 ± 0.8 | 5 ± 4 |
| SHAM | 60 ± 8 | 4.7 ± 1.1 | 12 ± 7 | 58 ± 10 | 1.7 ± 1.0 | 5 ± 4 |
| | Shock* | | | | | |
| HES | 52 ± 10 (0.85 ± 0.09) | 0.8 ± 0.4 (0.19 ± 0.12) | 2 ± 1 (0.14 ± 0.10) | 56 ± 12 (0.91 ± 0.11) | 0.4 ± 0.3 (0.24 ± 0.14) | 1 ± 1 (0.21 ± 0.15) |
| PEG-Alb | 49 ± 9 (0.86 ± 0.11) | 0.5 ± 0.4 (0.17 ± 0.14) | 1 ± 1 (0.11 ± 0.08) | 58 ± 11 (0.92 ± 0.11) | 0.5 ± 0.3 (0.26 ± 0.12) | 1 ± 1 (0.23 ± 0.18) |
| SHAM | 52 ± 9 (0.87 ± 0.10) | 0.7 ± 0.3 (0.21 ± 0.11) | 2 ± 1 (0.16 ± 0.12) | 52 ± 12 (0.91 ± 0.06) | 0.5 ± 0.4 (0.27 ± 0.16) | 1 ± 1 (0.25 ± 0.15) |
| | Resuscitation** | | | | | |
| HES | 55 ± 12 (0.94 ± 0.12) | 1.5 ± 1.0 (0.48 ± 0.18) | 4 ± 3 (0.36 ± 0.24) | 58 ± 14 (0.94 ± 0.17) | 0.6 ± 0.4 (0.46 ± 0.20) | 2 ± 2 (0.41 ± 0.27) |
| PEG-Alb | 57 ± 11 (0.97 ± 0.10) | 2.7 ± 1.3 (0.67 ± 0.19) | 7 ± 5 (0.62 ± 0.34) | 60 ± 12 (0.96 ± 0.14) | 0.9 ± 0.5 (0.57 ± 0.28) | 3 ± 2 (0.53 ± 0.29) |
| SHAM | 49 ± 12§ (0.78 ± 0.09) | 0.8 ± 0.4 (0.26 ± 0.19) | 2 ± 2 (0.14 ± 0.12) | 51 ± 14§ (0.89 ± 0.10) | 0.4 ± 0.4 (0.16 ± 0.14) | 1 ± 1 (0.12 ± 0.14) |

Values are means ± SD; (Relative change from baseline).
*all parameters are different from baseline;
**RBC velocity and flow were different from baseline in all groups.
§significant different as compared to baseline.
($P < 0.05$)

TABLE 3

| Rheological properties after 90 min resuscitation | | | |
|---|---|---|---|
| | Blood Viscosity* cp | Plasma Viscosity* cp | Plasma COP* mmHg |
| Non-diluted Blood | 4.2 | 1.2 | 17.8 |
| HES | 2.1 | 1.1 | 16.3 |
| PEG-Alb | 2.0 | 1.4 | 18.7 |
| SHAM | 2.6 | 1.0 | 14.6 |

*Shear rate of 160 s−1 at 37° C.; COP, colloid osmotic pressure at 27° C. Hematocrits are presented in Table 2.

IV. Discussion

A principal finding of this study is that resuscitation with PEG-Alb and HES provide an initial identical recovery of systemic and microvascular conditions. This process lasts for about 15 minutes after resuscitation, at which time a trend develops that leads to differences in outcome between the two materials which become statically significant 30 minutes after resuscitation. Microvascular arteriolar flow and tissue pH appear to be the earliest indicators of this trend, showing that the divergence in outcome initiates 10 minutes after resuscitation.

A probable cause for the noted difference in recovery could be related to the combined effects due to lack of sustained recovery of arteriolar flow and FCD which hinders the progressive washout of metabolites from the tissue, preventing lactic acid from returning to normal levels and causing the incomplete restoration of positive levels of base excess, conditions mirrored by the limitation of the normalization of pH, which for HES resuscitation ceases 15 minutes after resuscitation.

The improved resuscitation observed using PEG-Alb in comparison with HES in peripheral skeletal muscle tissue should be paralleled by effects in the heart muscle, thus leading to sustained improved cardiac function after resuscitation with PEG-Alb. This is also evidenced by the extended maintenance of blood pressure and improvement of arteriolar flow, both indicative of the recovery of cardiac output (36).

The initial similarity of response observed for both materials should be due to the rapid blood volume restoration complemented by auto transfusion. Hydroxyethyl starch solutions (HES, Pentaspan, in clinical use as plasma expanders) are modified natural polymers of amylopectin (200 kDa, molar substitution 0.50, C2:C6 ratio 4.6, Braun Medical, Irvine, Calif.). In the circulation starch degrades into components smaller than the renal threshold (~55 kDa) within minutes by breakage of the alpha 1-4-bond by alpha amylase, a process that is slowed by the substitution of the —OH group with hydroxyethyl groups (—OCH$_2$CH$_2$OH). PEG-Alb is stable for a longer period, with a half life in excess of 4 hours, and upon degradation the remaining albumin (~50% of the molecular material) remains oncotically active for a period similar to that of the native albumin in blood (~16 hr). HES has a higher molecular weight, however its distribution is broad with a approximately 10% fraction reported to be below 55 kDa. It should be noted that this fraction is indicated for the product at the time of manufacture, while according to Dieterich et al. (37) the material degrades in storage. Thus the filtrable fraction is not precisely known at the time of the experiment, but is likely to be significant, and will increase within minutes of injection. Conversely the distribution of PEG-Alb has a sharp cut off at 69 kDa, the molecular weight of albumin.

During ischemic hypoxia (induced by hemorrhagic shock) ATP formation from oxidative phosphorylation is inhibited completely due to oxygen deprivation. Various studies show the relationships between pH and loss of cell viability (38). Hemorrhage and shock extend and/or increase acidosis placing the cells in mildly acidic pH prolonging cell survival. Finally, the group without resuscitation did not significantly increase pH during the observation period, showing that tissue did not undergo irreversible cell injury.

Flow and FCD are the first parameters that show the divergence in outcome as resuscitation progresses, however MAP continues to increase and shows the beginning of the divergence in trend about 5 min later. The variability in the data is relatively large, however the trend for MAP and arteriolar blood flow show that these parameters become statistically significantly different at 30 min and 15 min after resuscitation respectively. Lowering of arteriolar flow in the presence of increased blood pressure suggests that resuscitation with HES causes some degree of vasoconstriction, or the lack of continued relaxation of the arterial circulation in a district not accessible to the present observations. This concept is further supported by the similarity in the temporal behavior of FCD and arteriolar flow. In previous studies by Cabrales et al. (33), it was shown that FCD is a direct and linear function of capillary pressure. The noted lowering of FCD at about 10 min after resuscitation is likely due to the decrease of capillary pressure, and may be a consequence of vasoconstriction.

The trend of FCD suggests that PEG-Alb restores capillary pressure, while resuscitation with HES indicates that after an initial 10 min transient where all parameters follow the same trajectory as PEG-Alb resuscitation, there is an interruption in the resuscitation process that may be related to a vasoconstrictor stimulus. A possible cause for this is a deficiency in volume regulation that may occur as the low molecular weight components of HES extravasate, lowering COP and the osmotic effect that drives autotransfusion from blood to the tissue compartment.

Figure 18:
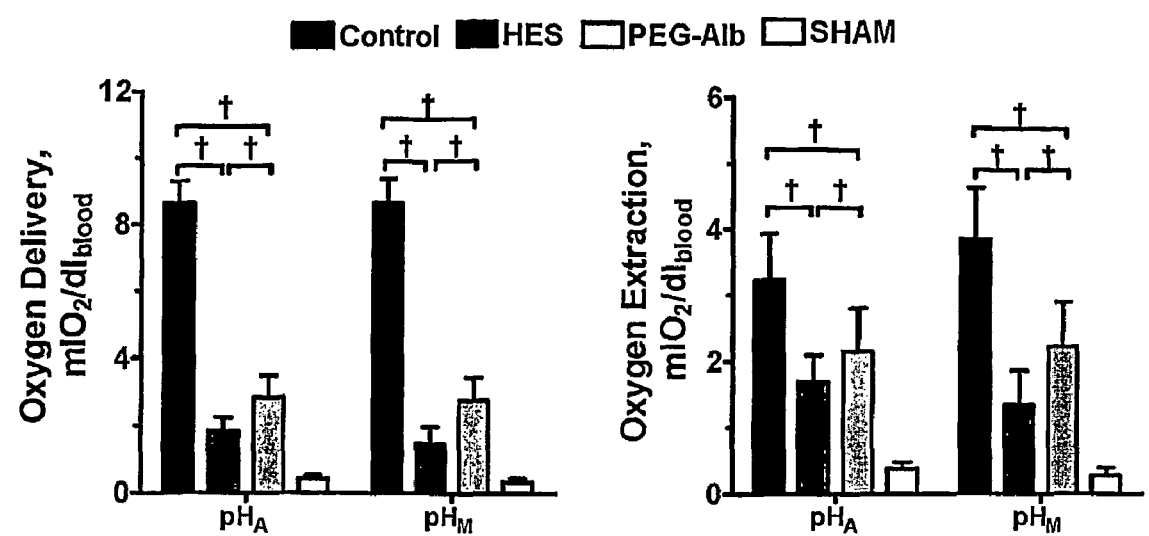
FIG. 18. Oxygen extraction and delivery for microcirculation and arteriolar pH. The use of microcirculation or arterial pH to correct $pO_2$ in the evaluation of oxygen delivery and release did not change the results of the study. The maximum change on the oxygen delivery and release found using the pH correction was less than 20%. †: significantly different between HES and PEG-Alb (P<0.05).

The present study provides an integrated view of the relation between blood and tissue $pO_2$ and pH. Conditions of tissue hypoxia prevalent in hemorrhagic shock promote the generation of lactic acid, which regulates pH in the muscle. The present results show that the restoration of oxygen delivery and release in the microcirculation (FIG. 18) caused by PEG-Alb resuscitation is a factor in controlling acidosis, and therefore tissue pH. This effect is ultimately related to the improvement of FCD, which facilitates the extraction of the slowly diffusing lactic acid from the tissue. Therefore the regulation of pH in the muscle is intertwined with FCD, oxygen availability and the corresponding production of lactic acid. A corollary of this assertion is that the continuos monitoring of pH reflects the evolution of tissue oxygenation.

Figure 19:
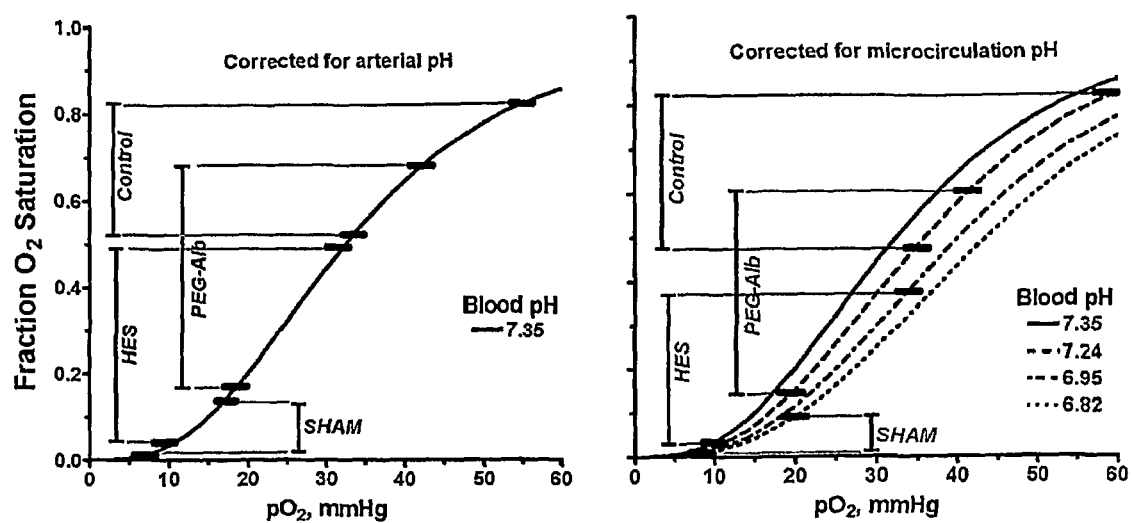
FIG. 19. Effect of pH on hamster blood oxygen saturation. Hemorrhage decreased pH and changed hemoglobin oxygen affinity (Bohr effect). The use of the microcirculation or arterial pH and corrected $pO_2$ to determine blood hemoglobin oxygen content did not change the results of the study. The maximum change on the oxygen saturation levels due to the pH correction was less than 20%.

These studies were in part carried out to determine the effect of changes in pH on the determination of oxygen transport parameters. This is a concern in hemorrhage where pH undergoes significant changes. These changes affect both the PQM oxygen measurement procedure, since the oxygen quenching constant is pH dependant, as well as the conversion from $pO_2$ determination to hemoglobin oxygen saturation, since pH shifts the position of the oxygen dissociation curve. The finding that pH corrections in hemorrhagic shock shown in FIG. 19 causes at most a 10% change in the data suggests that this parameter is not determinant in evaluating oxygen transport properties in the microcirculation.

The pH probe does not penetrate the cell membrane (24) and therefore it causes minimal interference with cellular metabolism and can be used repeatedly. Furthermore, as in the case of oxygen measurements the technique is intrinsically independent of dye concentration, and therefore the optical characteristics of the tissue and the illumination method.

In conclusion, the use of HES and PEG-Alb in shock resuscitation show that intravascular persistence and maintenance of blood volume appear to play a key role in the early stages of resuscitation. A notable finding is that subtle differences in physical properties between volume replacement solutions manifest themselves early on in the resuscitation process. Most recent ideas about resuscitation in humans suggest that the critical time in which to implement therapy is within a period termed the "golden hour". The present findings suggest that outcome may be in part predetermined by events taking place within a period of minutes upon commencement of the resuscitation process, and therefore treatment should be instituted on the basis of data derived as close as possible to the time at which hemorrhagic shock conditions are established. The present results derived from data obtained at the microscopic tissue level shows an evolution of local parameters that is not evident when monitoring systemic data over a period of one and a half hours. This finding is particularly relevant in experimental studies where the indicators proposed, like local pH, FCD, and microvascular parameters can be measured in the tissue, a situation not reproducible in clinical practice. Finally, this study indicates that PEG-Alb has superior resuscitation capacity in the short term when compared to HES.

In summary, this aspect of the present invention is based on the concept that in normovolemic reductions of blood, hemoglobin (Hb) levels lower than those associated with present transfusion triggers do not limit oxygen availability to the tissue; however, microvascular function fails because when conventional plasma expanders are mixed or substituted for blood, the viscosity of blood and plasma in the circulation is too low. The transfusion of PEGylated albumins as described herein produces a baseline level of blood/plasma viscosity that insures in the presence of blood losses that reduce oxygen carrying capacity beyond the transfusion trigger, central blood pressure remains close to normal, leading to normal capillary pressure, which is necessary to insure normal functional capillary density (FCD). This effect cannot be attained by increasing blood pressure via vasoconstriction, since this hinders the transmission of central pressure to the capillary network. The critical issue in restoring tissue to normalcy after hemorrhage is to attain adequate passage of red blood cells (RBCs) through the capillaries. This results from: 1) capillary pressurization, i.e., adequate intravascular pressure; 2) the presence of a longitudinal pressure gradient, which coupled to local microvascular blood viscosity establishes an adequate level of shear stress on the endothelium; and 3) maintenance of near normal levels of shear due to increased plasma viscosity promoting formation of nitric oxide (NO) by the endothelium, vasodilatation and increased perfusion. All of these effects are attained using PEG-Albumin as a plasma expander in resuscitation from hemorrhagic shock. Normalized flow, shear stress and capillary pressure consequent to the use of PEG-Albumin as a plasma expander are required for facilitating the passage of RBCs through the capillaries and thus maintaining FCD. The restoration of blood volume with PEG-Albumin provides for normal systemic and microvascular conditions up to the loss of ¾ of the red blood cell mass. Conventional plasma expanders only sustain systemic and microvascular conditions up to a loss of ½ of the red blood cell mass. Since blood transfusion protocols are used to restore oxygen carrying capacity after a loss of ½ of the red blood cell mass, the use of PEG albumin will significantly reduce the use of blood to remedy loss of oxygen carrying capacity. Accordingly, PEG-Albumin can be used to extend the capacity of conventional plasma expander and remedy blood losses between ½ and ¾ of the original red blood cell mass. The therapeutic result to be obtained is superior to the use of blood, or other plasma expanders, since other materials and blood do not restore FCD in the short term.

REFERENCES

1. Shoemaker, W. C., Appel, P. L., and Kram, H. B. 1998. Prospective trial of supranormal values of survivors as therapeutic goals in high-risk surgical patients. *Chest* 94:1176-1186.
2. Porter, J. M., and Ivatury, R. R. 1998. In search of the optimal end points of resuscitation in trauma patients. *J Trauma* 44:908-914.
3. Ivatury, R. R., Simon, R. J., and Islam, S. 1996. A prospective randomized study of end points of resuscitation after major trauma: global oxygen transport indices versus organ-specific gastric mucosal pH. *J Am Coll Surg.* 183: 145-154.
4. Sato, Y., Weil, M. H., and Tang, W. 1997. Esophageal PCO2 as a monitor of perfusion failure during hemorrhagic shock. *J Appl Physiol* 82:558-562.
5. Beilman, G. J., and Cerra, F. B. 1996. The future: monitoring cellular energetics. *Crit Care Clin.* 12:1031-1042.
6. Powell, C. C., Schultz, S. C., and Burris, D. G. 1995. Subcutaneous oxygen tension: a useful adjunct in assessment of perfusion status. *Crit Care Med* 23:867-873.
7. Zhang, H., Rogiers, P., De Backer, D., Spapen, H., Manikis, P., Schmartz, D., and Vincent, J. L. 1996. Regional arteriovenous differences in P(CO2) and pH can reflect critical organ oxygen delivery during endotoxemia. *Shock* 5:349-359.
8. Kerger, H., Saltzman, D. J., Menger, M. D., Messmer, K., and Intaglietta, M. 1996. Systemic and subcutaneous microvascular $pO_2$ dissociation during 4-h hemorrhagic shock in conscious hamsters. *Am J Physiol* 270:H827-H836.
9. Wettstein, R., Cabrales, P., Erni, D., Tsai, A. G., Winslow, R. M., and Intaglietta, M. 2004. Resuscitation from hemorrhagic shock with MalPEG-albumin: comparison with MalPEG-hemoglobin. *Shock* 22:351-357.
10. Wettstein, R., Tsai, A. G., Erni, D., Lukyanov, A. N., Torchilin, V. P., and Intaglietta, M. 2004. Improving microcirculation is more effective than substitution of red blood cells to correct metabolic disorder in experimental hemorrhagic shock. *Shock* 21:235-240.
11. Cabrales, P., Tsai, A. G., and Intaglietta, M. 2004. Hyperosmotic-hyperoncotic vs. hyperosmotic-hyperviscous small volume resuscitation in hemorrhagic shock. *Shock* 22:431-437.
12. Cabrales, P., Intaglietta, M., and Tsai, A. G. 2005. Increase plasma viscosity sustains microcirculation after resuscitation from hemorrhagic shock and continuous bleeding. *Shock.*
13. Guyton, A. C. 1996. Local Control of Blood Flow by the Tissues, and Humoral Regulation. In *Textbook of Medical Physiology*. Philadelphia: W.B. Saunders. 199-207.
14. De Blasi, R. A., Ferrari, M., Antonelli, M., Conti, G., Almenrader, N., and Gasparetto, A. 1996. O2 consumption-O2 delivery relationship and arteriolar resistance in the forearm of critically ill patients measured by near infrared spectroscopy. *Shock* 6:319-325.
15. Rixen, D., Raum, M., Holzgraefe, B., Schafer, U., Hess, S., Tenhunen, J., Tuomisto, L., and Neugebauer, E. A. 2002. Local lactate and histamine changes in small bowel circulation measured by microdialysis in pig hemorrhagic shock. *Shock* 18:355-359.
16. Carsten, J. 2001. Current aspects of lactate exchange: lactate/H+ transport in human skeletal muscle. *Eur J Appl Physiol* 86:12-16.
17. Aalkjier, C., and Peng, L. 1997. pH and smooth muscle. *Acta Physiol Scand* 161:557-566.
18. Brantigan, J. W., Ziegler, E. C., and Hynes, K. M. 1974. Tissue gases during hypovolemic shock. *J Appl Physiol.* 37:117-122.
19. Moolenaar, W. H., Y., T. R., Van Der Saag, P. T., and De Laat, S. W. 1983. Na+/H+ exchange and cytoplasmic pH in the action of growth factors in human fibroblasts. *Nature Lond.:*304: 645-648.
20. Colantuoni, A., Bertuglia, S., and Intaglietta, M. 1984. Quantitation of rhythmic diameter changes in arterial microcirculation. *Am J Physiol* 246:H508-H517.
21. Endrich, B., Asaishi, K., Götz, A., and Messmer, K. 1980. Technical report: A new chamber technique for microvascular studies in unanaesthetized hamsters. *Res Exp Med* 177:125-134.
22. Tsai, A. G., Friesenecker, B., McCarthy, M., Sakai, H., and Intaglietta, M. 1998. Plasma viscosity regulates capillary perfusion during extreme hemodilution in hamster skin fold model. *Am J Physiol* 275:H2170-H2180.
23. Hanson, K. M., Behne, M. J., Barry, N. P., Mauro, T. M., Gratton, E., and Clegg, R. M. 2002. Two-photon fluorescence lifetime imaging of the skin stratum corneum pH gradient. *Biophys J* 83:1682-1690.
24. Helmlinger, G., Yuan, F., Dellian, M., and Jain, R. K. 1997. Interstitial pH and pO2 gradients in solid tumors in vivo: high-resolution measurements reveal a lack of correlation. *Nat Med* 3:177-182.
25. Street, D., Bangsbo, J., and Juel, C. 2001. Interstitial pH in human skeletal muscle during and after dynamic graded exercise. *J Physiol* 537:993-998.
26. Dellian, M., Helmlinger, G., Yuan, F., and Jain, R. K. 1996. Fluorescence ratio imaging of interstitial pH in solid tumours: effect of glucose on spatial and temporal gradients. *Br J Cancer* 74:1206-1215.
27. Intaglietta, M., and Tompkins, W. R. 1971. System for the measurement of velocity of microscopic particles in liquids. *IEEE Trans Biomed* 18:376-377.
28. Lipowsky, H. H., and Zweifach, B. W. 1978. Application of the "two-slit" photometric technique to the measurement of microvascular volumetric flow rates. *Microvasc Res* 15:93-101.
29. Intaglietta, M., and Tompkins, W. R. 1972. On-line measurement of microvascular dimensions by television microscopy. *J Appl Physiol* 32:546-551.
30. Kerger, H., Groth, G., Kalenka, A., Vajkoczy, P., Tsai, A. G., and Intaglietta, M. 2003. $pO_2$ measurements by phosphorescence quenching: characteristics and applications of an automated system. *Microvasc Res* 65:32-38.
31. Pawlowski, M., and Wilson, D. F. 1992. Monitoring of the oxygen pressure in the blood of live animals using the oxygen dependent quenching of phosphorescence. *Adv Exp Med Biol* 316:179-185.
32. Sinaasappel, M., and Ince, C. 1996. Calibration of Pd-porphyrin phosphorescence for oxygen concentration measurements in vivo. *J Appl Physiol* 81:2297-2303.
33. Cabrales, P., Tsai, A. G., and Intaglietta, M. 2004. Microvascular pressure and functional capillary density in extreme hemodilution with low and high plasma viscosity expanders. *Am J Physiol Heart Circ Physiol* 287:H363-H373.
34. Lipowsky, H. H., and Firrell, J. C. 1986. Microvascular hemodynamics during systemic hemodilution and hemoconcentration. *Am J Physiol* 250:H908-H922.

35. Acharya, A. S., Manjula, B. N., and Smith, P. 1996, New York. Patent. Hemoglobin crosslinkers. Albert Einstein College of Medicine of Yeshiva University. (U.S. Pat. No. 5,585,484), 1-16.
36. Jan, K. M., Heldman, J., and Chien, S. 1980. Coronary hemodynamics and oxygen utilization after hematocrit variations in hemorrhage. *Am J Physiol* 239:H326-H332.
37. Dieterich, H. J. 2003. Recent developments in European colloid solutions. *J Trauma* 54:S26-30.
38. Gores, G. J., Nieminen, A.-L., Wray, B. E., B., H., and J., L. J. 1989. Intracellular pH during "Chemical Hypoxia" in Cultured Rat Hepatocytes. *J. Clin. Invest.* 83:386-396.

Example III

Cardiac Normalization Using Peg-Albumin

I. Introduction

Cardiac arrhythmias during anaesthesia and surgery occur in up to 86% of patients. Many are of clinical significance and therefore their detection is of considerable importance. As disclosed herein, intravenous infusion of PEG-Albumin has properties as a heart rate and cardiac output stabilizer, establishing the use of PEG-Albumin as a treatment for acute ventricular arrhythmias.

II. Methods and Results

The acute antiarrhythmic effect of PEG-Albumin was assessed using epinephrine-, digitalis-, microspheres injections- and calcium and potassium channels blocker-induced hamster ventricular arrhythmia models. Intravenous administration of PEG-Albumin (2.5% PEG-Albumin, 5% of blood volume) reduced the incidence of the ventricular arrhythmias in all models except for the calcium and potassium channel blockers. The antiarrhythmic effect on epinephrine-induced arrhythmia was potent and long-lasting, while those on the other arrhythmia models were weak and transient. The direct cardiovascular effects were assessed using Golden Syrian Hamsters kept under light anesthesia (continuous infusion of 50 mg/ml pentobarbital at 0.5 mg/min/kg body weight). The depth of anesthesia was regulated by tolerance of a noxious reflex due to pinching of the hind paw but no nonaversive reflexes (palpebral, corneal and jaw reflex). Cardiac information was recorded using continuous 3 leads electrocardiogram (ECG). The intravenous administration of PEG-Albumin decreased sinoatrial automaticity and partially normalized ventricular contraction, while it increased the duration of the monophasic action potential.

III. Discussion

These results show that PEG-Albumin possesses multiple electrophysiological properties and that the effects related to a sustaining of myocardial perfusion and cell membrane are relevant in causing antiarrhythmic activity. Consequently PEG-Albumin is proposed to be formulated in the range of 2.5-5.0% concentration by weight in saline and delivered as a bolus intravenously for the purpose of stabilizing cardiac activity, and controlling heart arrhythmias. The causal link between the electrophysiological properties and the antiarrhythmic action is hypothesized to be related to the polarization/de-polarization of ionic channels in the endothelium due to the hydration of PEG-Albumin.

Potential applications: PEG-Albumin may have the most useful function intraoperative as a valuable alternative to treat cardiac arrhythmias and heart rate anomalies. During anaesthesia and surgery PEG-Albumin can be used for treating arrhythmia, for example transient supraventricular and ventricular tachycardias due to sympathetic stimulation during laryngoscopy and intubation, and bradycardias produced by surgical manipulation resulting in vagal stimulation, where severe bradycardia and asystole may result. Cardiac arrhythmias are more common in children because the sympathetic innervation of the heart is immature and vagal tone predominates. Bradycardias are most commonly seen in ophthalmic surgery due to the oculocardiac reflex. Generally the heart rate will improve when the surgical stimulus is removed. Atrial fibrillation is common during thoracic surgery.

PEG-Albumin likely will aid recovery from pathologies that may cause changes in cardiac rhythm, e.g.: halothane and nitrous oxide may cause junctional rhythms; drugs increasing heart rate include ketamine, ether, atropine and pancuronium; drugs decreasing heart rate include opioids and beta blockers; and cardiac disease, hypoxia, acidosis, hypercarbia (raised $CO_2$ level) and electrolyte disturbances increase the presence of arrhythmias.

PEG-Albumin is proposed to constitute a new class of therapeutic material that can be used for the treatment of heart arrhythmias and cardiac dysfunctions.

Example IV

PEG-Albumin: a Plasma Expander with Positive Cardiac Effects Mediated Via Repair/Protection of the Glycocalyx I. Introduction Polyethylene glycol conjugated albumin (PEG-Alb) improves microcirculatory function in experimental models of extreme hemodilution and hemorrhagic shock; moreover, it provides an extended and sustained recovery period compared to conventional plasma expanders (e.g., albumin, hetastarch and dextran). During resuscitation from hemorrhagic shock, PEG-Alb significantly improves functional capillary density and capillary perfusion as a consequence of maintaining a higher systemic blood pressure, capillary pressure and cardiac output. Similar physiological consequences were obtained with hyperviscous fluids (up to viscosity of 9 cp), which increased shear stress interaction with the endothelium resulting in increased mechanotransduction and thus improved microvascular perfusion.

Since PEG-Alb is not much different in viscosity from plasma, 1.7 and 1.2 cp respectively, PEG-Alb was hypothesized to interact with the surface of the endothelium in other ways to produce biomechanical effects. When the microcirculation is subjected to hypoxia and anemia, the glycocalyx associated with the cellular surface is damaged resulting in an increased vascular permeability.

II. Methods and Results

Studies were performed in hamsters using a PEG-human serum albumin conjugate, hexa thiocarbamoyl phenyl PEG-5K albumin [(TCP-PEG5K)$_6$-human serum albumin]. To study the effects of PEG-Albumin on the heart, two protocols were used: 1) rapid hemorrhage (40% of the blood volume in 2 mins) and 2) coronary artery ligation. Additionally the interaction of PEG-Alb with the glycocalyx was studied by partial enzymatic breakdown (hyaluronase) of the glycocalyx followed by a restoring/repairing of its integrity by a small intravenous dosing of PEG-Alb (10% of the blood volume).

ST-segment elevation, indicative of an ischemic myocardium, produced by rapid hemorrhage (40% of the blood volume in 2 mins) demonstrated the ability of PEG-Alb to restore a normal ECG which was not obtained with 10% human serum albumin. Similar results were obtained with a coronary artery ligation model when the animal was pretreated with PEG-Alb. Administering PEG-Alb prior to the enzymatic damage of the glycocalyx produced no changes in mean arterial pressure and heart rate demonstrating a protective effect. The degree of glycocalyx damage was established by measuring changes in vascular volume using a dual fluorescent marker technique.

III. Discussion

PEG-Alb interacts with the glycocalyx and has both restorative and protective effects depending on the time of administration relative to the occurrence of glycocalyx injury. Since these effects should take place throughout the vascular endothelium, they are likely to also occur in the heart and cause the noted improvements in cardiac function following PEG-Alb administration.

HexaPEGylated human serum albumin generated by the reaction of thiocyanato phenyl PEG-5K with albumin has been used in these studies. The product, PEGylated albumin, could be stored either as a lyophilized material or as a solution of desired concentration of PEG-albumin adduct.

Example V

Transport of Nitric Oxide by PEGylated Albumin (Prophetic Example)

PEGylated albumin (PEG-Alb) is unique in causing vasodilatation in conditions of anemia, low viscosity, and low oxygen tension in the absence of demonstrated increased oxygen transport capacity or increased blood and plasma viscosity leading to increased mechano transduction.

This property of PEG-Alb is believed to be unique to the process of attaching PEG to the surface of the protein molecule. The chemical process that leads to pegylation of albumin involves the thiolation of the surface amino groups leading to the production of extra thiol groups on the protein surface. Thiol groups have been implicated with the transport of nitric oxide (NO) from high concentration regions of the circulation, like the aortic wall, to the lower NO concentration regions of the microcirculation. In this process PEG-Alb provides a source of extra thiols when the chemical process of pegylation does not neutralize all active sites generated on the albumin by thiolation. These mechanisms have been proposed to occur in normal blood and to be a part of the regulatory control of ischemia via dilation and increased perfusion. According to this mechanism, the same process is enhanced by the presence of unreacted thiols on the surface of PEG-Alb. Therefore, the enhancement of an NO transporting mechanism explains the unusual vasodilatory capacity of PEG-Albumin when pegylation is made via thiolation.

In support of this role, according to Cabrales et al. (2005) extreme hemodilution with PEG-Albumin and PEG-Hemoglobin produce the same microvascular and systemic effects, namely increasing cardiac index above baseline, vasodilating arterioles and increasing functional capillary density to the same level.

These effects cannot be achieved with conventional plasma expanders such as Dextran 70 kDa and human serum albumin. Furthermore, they are not due to increased oxygen carrying capacity and delivery since PEG-albumin does not carry oxygen and therefore does not deliver extra oxygen to the tissue as evidenced by tissue $pO_2$ being the same as for dextran 70 kDa and human serum albumin used in identical experiments.

PEG albumin therefore is a unique plasma expander that enhances NO distribution in the circulation, and by virtue of the PEG conjugation, has a prolonged vascular retention time, when compared with albumin, as well as additional plasma expansion capacity due to increased colloidal osmotic pressure.

REFERENCE

Cabrales P, Tsai A G, Winslow R M, Intaglietta M (2005) Extreme hemodilution with PEG-hemoglobin vs. PEG-albumin. Am J Physiol Heart Circ Physiol. 289(6): H2392-400. Epub 2005 Jul. 15.

Example VI

PEGylation of Albumin

Additional description is provided of examples of PEGylated albumins that can be used in the present invention.

Thiolation mediated maleimide chemistry based PEGylation of albumin was carried out with maleimide-phenyl-PEG-5000 (Mal-Phe-PEG-5K), using reaction conditions comparable to that used for the PEGylation of Hb to generate non-hypertensive Hb. Albumin has 35 half-cystine residues; all of which except one at position 34 (Cys-34) are involved in intra-molecular disulfide bonds. Therefore, more thiol groups were introduced onto the protein using 2-iminothiolane to facilitate the attachment of Mal-Phe-PEG-5K chains.

Albumin has been subjected to PEGylation under two different reaction conditions to generate two PEGylated products with different levels of PEGylation. For the preparation of both of these samples, the maleimide chemistry based PEGylation was used in the one step mode followed by tangential flow filtration of the PEGylated albumin to remove the excess PEG reagent. For the first preparation, reaction conditions were optimized to generate a product with an average of six PEG-chains per molecule as determined by the mass spectral analysis. The hydrodynamic volume of the hexaPEGylated albumin is slightly larger than that of hexa PEGylated Hb. This hexa-PEGylated albumin, $(SP-PEG5K)_6$-albumin, exhibits a viscosity of 2.4 cp and a colloidal osmotic pressure of 37 mm Hb. Thus, the viscosity of a 4 g % solution of hexa-PEGylated albumin is slightly lower than that of a 4 g % solution of hexa-PEGylated Hb [$(SP-PEG5K)_6$-Hb]. But the colloidal osmotic pressure of a 4 g % solution of $(SP-PEG5K)_6$-albumin is noticeably lower than that of the hexa PEGylated Hb.

The molecular mass of Hb and of albumin are nearly identical, but the hydrodynamic volume of albumin is slightly higher than that of Hb as reflected by size exclusion chromatography. The difference in the hydrodynamic volume is consistent with the fact that the molecular radius of albumin as determined by light scattering is around 4.0 nm whereas that of Hb is only around 3.0 nm. Thus, the six copies of PEG-5K chains conjugated to Hb in $(SP-PEG5K)_6$-Hb by thiolation mediated conservative PEGylation are more efficient in increasing the colloidal osmotic pressure of Hb than the six copies of PEG-5K chains conjugated by the same conjugation chemistry to albumin. Given the difference in the molecular surface area of Hb and albumin, which is a direct consequence of the difference in the molecular radius of the two unPEGylated parent proteins, the results suggest that there is a correlation between the number of PEG-chains of a given molecular mass on a given molecular surface area, i.e., there is a correlation between the density of PEG-units in a given molecular volume and the colloidal osmotic pressure of the PEGylated protein.

Another preparation of PEGylated albumin that carries on an average 12 copies of the PEG-5K chains per mole, [(SP- PEG5K)$_{12}$-albumin], has also been prepared. On size exclusion chromatography the (SP-PEG5K)$_{12}$-albumin elutes slightly ahead of (SP-PEG5K)$_6$-albumin. Consistent with the presence of higher number of copies of PEG-5K on the molecular surface as compared to that of (SP-PEG5K)$_6$-albumin, the viscosity and the colloidal osmotic pressure of (SP-PEG5K)$_{12}$-albumin are higher, being 3.7 cp and 102 mm Hg respectively, for a 4 g % solution. These results suggest that the correlation between the increase in the colloidal osmotic pressure of a protein as a function of the mass of PEG on a given molecular surface is nonlinear and increases in a exponential fashion, while the viscosity of the sample as a function of the PEGylation is more linear.

The propensity of the PEGylation reaction to endow PEGylated albumin with an enhanced molecular radius besides increased viscosity and colloidal osmotic pressure (COP) should lower filtration. Thus, the extravasation seen on transfusion with albumin solutions, particularly in some pathological conditions, should be reduced. Given the increased viscosity and COP, a lower concentration of PEGylated albumin needs to be used (relative to albumin) to maintain the same parameters.

(SP-PEG5K)$_6$-albumin and (SP-PEG-5K)$_{12}$-albumin with enhanced molecular size (hydrodynamic volume), viscosity and colloidal osmotic pressure can serve as better plasma expanders than albumin itself, especially under some pathological conditions wherein there is an increase in the leakiness of the blood vessels for albumin causing edema. Since the drug binding activity of these PEGylated albumins are not significantly influenced by PEGylation, these products are expected to function better than other conventional crystalloid or colloidal plasma expanders that are currently in use.

The ε-amino groups of the Lys residues of proteins can also be thiolated using dithiobis(succinimidyl propionate) (DTSP) or dithiobis(sulfosuccinimidyl propionate) (DTSSP) or dithiobispropionimidate. In this protocol, the protein is thiolated at the ε-amino groups by the acylation chemistry and accordingly the thiolation of the protein is accompanied by a loss of the positive charge of the ε-amino groups derivatized. The protein is first derivatized with the bifunctional disulfide bridged active ester under conditions wherein, predominantly, a monofunctional modification of the protein is accomplished. The excess reagent is separated from the modified protein, and the modified protein is converted to a thiolated protein in the presence of maleimide using non-thiol reducing agents, for example, tris carboxyethyl phosphine. This thiolation mediated PEGylation protocol has been developed to generate a new class of PEGylated proteins.

Since the solution properties of the PEGylated protein are not a direct consequence of PEG mass, the charge of the amino group influences the consequence of PEGylation. Accordingly, one can choose the PEGylation strategy to manipulate (customize) the solution properties of PEGylated albumin. Instead of using dithiosuccinimidyl propionate (acylation chemistry), one could use dithiopropionimidate (amidation chemistry) to achieve the thiolation without altering the positive charge at the site of the attachment of the extension arm.

The flexibility of the thiolation mediated PEGylation protocol can be increased by using other functionalized PEG reagents specific for sulfhydryl groups, e.g. iodoalkylamide PEG derivatives, vinyl sulfone PEGs and mixed disulfides of PEG.

Besides PEGylated albumin generated by thiolation mediated PEGylation, PEG-albumin has also been generated using isothiocyanato chemistry based PEGylation.

Both the conservative and non-conservative thiolation protocols discussed in this disclosure engineer an "extension arm" between the protein and the PEG-chain as compared to the simple nonconservative PEGylation that involves the formation of an isopeptide bond (PEG conjugating group) directly on the ε-amino group of the protein. The "extension arm" introduced between the PEG and protein appears to reduce the propensity of the PEG chain to endow the PEGylated protein with a higher viscosity and colloidal osmotic pressure.

The engineering of the extension arm also increases the accessibility of the newly introduced thiol groups. The flexibility of the thiolation protocol can be increased to manipulate the solution properties of PEGylated protein and/or accessibility of the new thiol groups by varying the length of the extension arm from 3 to 4, six to eight carbon atoms by using propionic acid, butyric acid, caproic acid or caprylic acid as the extension arm, using either acylation or amidation chemistry to attach the extension arm that has a thiol group at the distal end protected either as a symmetrical disulfide of a mixed disulfide. Dithiopyridyl group is used to generate a mixed disulfide that can be used for protein thiolation.

Thiocarbmoyl PEG albumin. Human serum albumin (0.5 mM) in 10 mM phosphate buffer was reacted with 5 mM (10 fold molar excess) of isothiocyanato PEG 5K at 4° C. either at pH 6.5 or at pH 9.2 overnight. The reaction mixture was subjected to tangential flow filtration against phosphate buffered saline, pH 7.4, to get red of the excess PEG reagent. The dialysis of the PEG reagent from the sample was followed by an FPLC analysis that monitored the absorbance at 210 nm and the refractive index of the effluent. The sample thus generated a high degree of molecular size homogeneity. The sample generated at pH 6.5 had about four groups while the one generated at pH 9.2 carried nearly 6 to 7 copies of PEG-5K chains.

Surface Decoration of Human Serum Albumin (HSA) with Multiple Copies of Polyethylene Glycol 5000 (PEG5K) Chains: Extension Arm Facilitated Conservative PEGylation. The reactivity and accessibility of the surface functional groups of proteins to macromolecular PEG-reagents are the two major factors that influence efficiency of PEGylation of proteins. A thiol-maleimide chemistry based, extension arm facilitated PEGylation protocol has been developed to overcome these limitations and applied to HSA to develop PEGylated HSA as a plasma volume expander. By controlling the concentration of HSA and of iminothiolane (a reagent that engineers the extension arm on surface amino groups with a thiol group at its distal end) the number of copies of PEG-chains coupled to HSA can be controlled. HexaPEGylated HSA has been generated to compare the chemical, biochemical and colligative properties of the material with that of vasoinactive, nonhypertensive hexaPEGylated Hb (Manjula et al., 2005). The one step PEGylation protocol wherein the maleimide PEG is present during thiolation is an improved protocol that avoids formation of thiolation induced oligomerization of HSA during PEGylation. Interestingly, PEGylation induced properties of hexaPEGylated HSA are distinct from those of hexaPEGylated Hb. The lower viscosity and colloidal oncotic pressure and higher hydrodynamic volume of PEGylated HSA compared to the hexaPEGylated HbA at comparable protein concentrations suggests that either the colligative properties of PEGylated protein are a correlate of the density of the PEG-chains on the molecular surface, or hexa PEGylated Hb dissociates to have a higher number of effective particles in solution. The simplicity and cost effectiveness of this PEGylation protocol makes this a candidate for large scale production of PEGylated HSA as a plasma volume expander.

REFERENCE

Manjula, B. N., Tsai, A. G., Intaglietta, M., Tsai, C-H., Ho, C., Smith, P. K., Perumalsamy, K., Kanika, N. D., Friedman, J. M., and Acharya, A. S. (2005) Conjugation of multiple copies of polyethylene glycol to hemoglobin facilitated through thiolation: Influence on hemoglobin structure and function. Protein J. 42: 133-146.

Thiolation of HexaPEGylated albumin. Thiocarbamoyl human serum albumin exhibits molecular properties comparable to that of hexaPEGylated human serum albumin generated by extension arm facilitated PEGylation, and is a good plasma expander just as the hexaPEGylated albumin that was generated by the extension arm facilitated maleimide chemistry based PEGylation. Accordingly, additional molecular properties can be introduced to PEGylated albumin to increase its clinical applications.

One such contemplated molecular property is to facilitate the transport of nitric oxide (NO) when the PEGylated albumin is in the plasma, i.e. to facilitate the transport of NO by PEGylated albumin by generating PEGylated and thiolated human serum albumin, where the thiol groups can transport NO as S-nitroso derivatives. Transport of NO by the protein thiols is an established mechanism for the transport of the oxygen. Reaction of iminothiolane with thiocarbomoyl PEG albumin generated the desired PEGylated thiolated human serum albumin.

Figure 20:
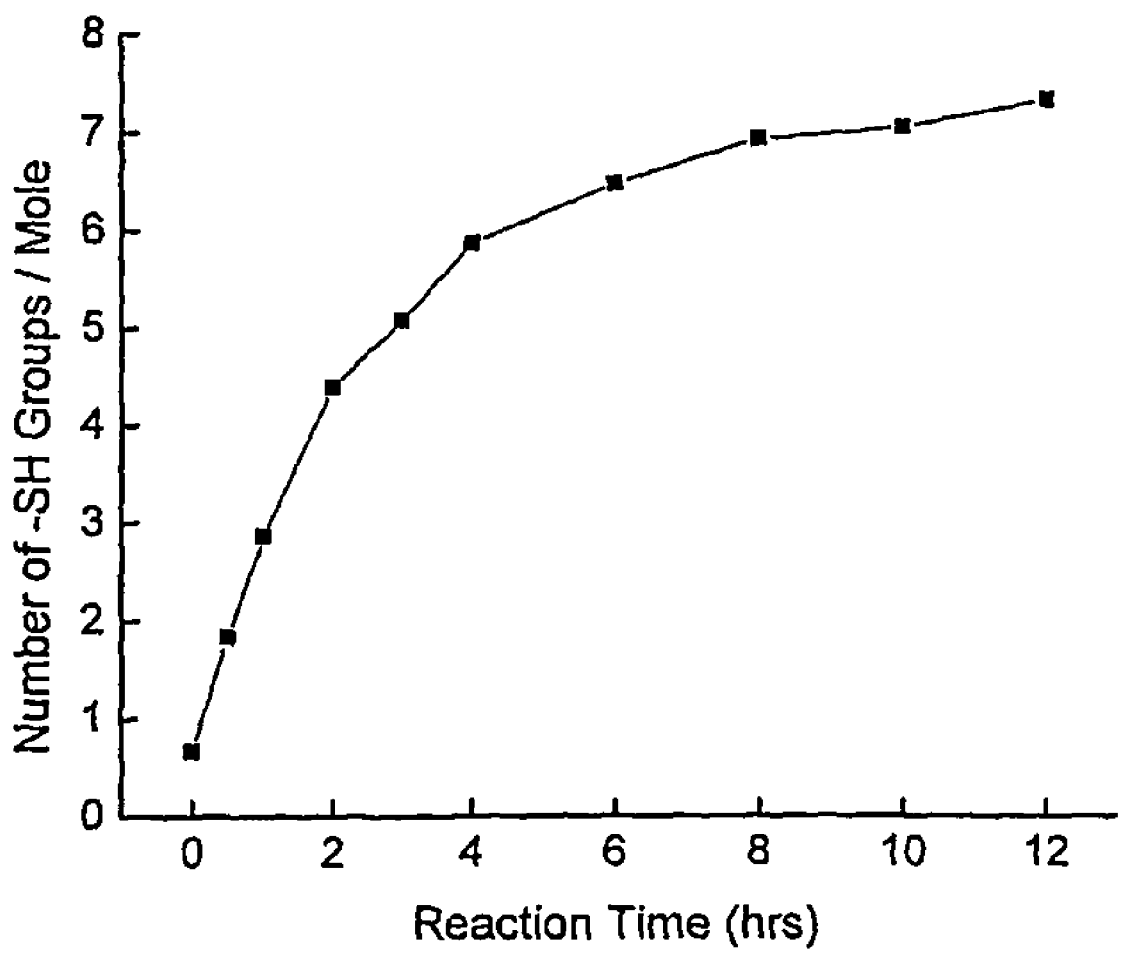
FIG. 20. Kinetics of thiolation of (Thiocarbamoyl Phenyl PEG-5K) human serum albumin.

FIG. 20 presents the kinetics of thiolation of the PEGylated protein with iminothiolane at a protein concentration of 0.5 mM and an iminothiolane concentration of 10 mM at pH 7.4 and 4° C. Stopping the reaction at a given time point generates the PEGylated product with the desired level of thiol groups. By increasing the concentration of iminothiolane to 40 mM, as many as nearly 20 thiol groups could be introduced per molecule.

Another molecular property that has been engineered into the PEGylated albumin is an added ability for the PEGylated molecule to scavenge free radicals in the circulatory system. Increased levels of free radicals is the consequence of oxidative stress in biological systems. Polynitroxylation of proteins is an approach that has been advanced to facilitate the scavenging of such free radicals. Covalent attachment of nitroxyl radicals is engineered onto PEGylated protein by the thiolation mediated maleimide chemistry based approach; a polynitroxylated PEGylated albumin has been prepared by reacting PEGylated albumin with maleimide proxyl (or maleimide tempol) in the presence of iminothiolane. In the present study, PEGylated polynitroxylated albumin has been now generated. Thus, these PEGylated albumin molecules can achieve both vasodilation and scavenging of free radical when in the circulation.

All publications mentioned herein are hereby incorporated in their entirety into the subject application. While the foregoing invention has been described in some detail for purposes of clarity and understanding, it will be appreciated by one skilled in the art, from a reading of the disclosure, that various changes in form and detail can be made without departing from the true scope of the invention set forth in the appended claims.

What is claimed is:

1. A method of treating cardiac arrhythmia in a subject having cardiac arrhythmia which comprises administering to the subject an amount of a PEGylated albumin effective to treat cardiac arrhythmia in the subject.

2. The method of claim 1, wherein the cardiac arrhythmia is a ventricular arrhythmia.

3. The method of claim 1, wherein the cardiac arrhythmia is an atrial arrhythmia.

4. The method of claim 1, wherein the albumin is human serum albumin or bovine serum albumin.

5. The method of claim 1, wherein the concentration of PEGylated albumin is 1.5 g/dL-5.0 g/dL.

6. The method of claim 5, wherein the PEGylated albumin is administered at a dose of 16 to 30 ml/kg body weight/hr.

7. The method of claim 1, wherein the PEGylated albumin has a molecular weight of about 130 kDa.

8. The method of claim 1, wherein 6-18 PEG chains are conjugated to albumin.

9. The method of claim 1, wherein each PEG chain of the PEGylated albumin has a molecular weight of 200 daltons to 20,000 daltons.

10. The method of claim 9, wherein each PEG chain has a molecular weight of 3,000 to 5,000 daltons.

11. The method of claim 1, wherein the PEGylated albumin has a molecular radius of 8-9 nm.

12. The method of claim 1, wherein the PEGylated albumin has a colloid osmotic pressure of 37-40 mm Hg.

13. The method of claim 1, wherein the PEGylated albumin has a viscosity of 2.0 to 4.0 cP.

14. The method of claim 1, wherein a polyethylene glycol (PEG) used to make the PEGylated albumin is a maleimide PEG, an alkylamide PEG, an iodoacetamide PEG, a p-nitro thio-phenyl PEG, a vinyl sulfone PEG, or a mixed disulfide PEG.

15. The method of claim 14, wherein the maleimide PEG is a maleimide phenyl PEG or a maleimide PEG comprising an alkyl linker.

16. The method of claim 1, wherein the PEG is attached to the albumin via a linker and/or an extension arm.

17. The method of claim 16, wherein the linker comprises an alkyl, aryl and/or heteroaryl group.

18. The method of claim 16, wherein the linker or extension arm comprises a δ-mercapto butyrimidyl chain or a γ-mercapto propylamide chain.

19. The method of claim 1, wherein the PEGylated albumin comprises a polyethylene glycol (PEG) attached to a thiolated amino group of albumin, and wherein the amino group is thiolated using dithiobis(sulfosuccinimidyl propionate) (DTSSP) or dithiobis(succinimidyl propionate) (DTSP) or dithiobispropionimidate.

20. The method of claim 1, wherein PEGylation of albumin does not alter the surface charge of albumin.

21. The method of claim 1, wherein the subject is undergoing anaesthesia and surgery.

22. The method of claim 1, wherein the concentration of PEGylated albumin is 2.5 g/dL.

23. The method of claim 22, wherein the PEGylated albumin is administered at a dose of 24 ml/kg body weight/hr.

24. The method of claim 1, wherein 12 PEG chains are conjugated to albumin.

25. The method of claim 1, wherein each PEG chain of the PEGylated albumin has a molecular weight of 5,000 daltons.

26. The method of claim 1, wherein administration of PEGylated albumin decreases sinoatrial automaticity, partially normalizes ventricular contraction, and increases the duration of the cardiac monophasic action potential.

27. The method of claim 1, wherein the cardiac arrhythmia is induced by a drug or by nerve stimulation during surgery or is associated with cardiac disease, hypoxia, acidosis, hypercarbia or an electrolyte disturbance.

* * * * *